(12) United States Patent
Benson et al.

(10) Patent No.: US 9,161,799 B2
(45) Date of Patent: Oct. 20, 2015

(54) SURGICAL IMPLANT SYSTEM AND METHOD

(71) Applicant: Warsaw Orthopedic, Inc., Memphis, TN (US)

(72) Inventors: Nicholas M. Benson, Cordova, TN (US); Larry T. McBride, Memphis, TN (US)

( * ) Notice: Subject to any disclaimer, the term of this patent is extended or adjusted under 35 U.S.C. 154(b) by 0 days.

(21) Appl. No.: 13/751,823

(22) Filed: Jan. 28, 2013

(65) Prior Publication Data

US 2014/0214086 A1    Jul. 31, 2014

(51) Int. Cl.
*A61B 17/88* (2006.01)
*A61B 17/16* (2006.01)
*A61B 17/17* (2006.01)
*A61B 19/00* (2006.01)

(52) U.S. Cl.
CPC ........... *A61B 17/885* (2013.01); *A61B 17/1655* (2013.01); *A61B 17/17* (2013.01); *A61B 19/5244* (2013.01); *A61B 17/1757* (2013.01); *A61B 2019/5255* (2013.01); *A61B 2019/5466* (2013.01)

(58) Field of Classification Search
CPC .. A16B 17/885; A16B 17/1655; A16B 17/17; A16B 19/5244
USPC ...................... 606/279, 191, 80; 600/202, 429
See application file for complete search history.

(56) References Cited

U.S. PATENT DOCUMENTS

| | | | |
|---|---|---|---|
| 6,021,343 A * | 2/2000 | Foley et al. | .................... 600/429 |
| 6,190,395 B1 | 2/2001 | Williams | |
| 6,198,961 B1 | 3/2001 | Stern et al. | |
| 6,235,038 B1 | 5/2001 | Hunter et al. | |
| 6,267,769 B1 | 7/2001 | Truwit | |
| 6,402,762 B2 | 6/2002 | Hunter et al. | |
| 6,468,202 B1 | 10/2002 | Irion et al. | |
| 6,477,400 B1 | 11/2002 | Barrick | |
| 6,478,802 B2 | 11/2002 | Kienzle et al. | |
| 6,491,699 B1 | 12/2002 | Henderson et al. | |
| 6,556,857 B1 | 4/2003 | Estes et al. | |
| 6,565,577 B2 | 5/2003 | Cosman | |
| 6,584,339 B2 | 6/2003 | Galloway et al. | |
| 6,585,651 B2 | 7/2003 | Nolte et al. | |
| 6,605,095 B2 | 8/2003 | Grossman | |
| 6,694,168 B2 | 2/2004 | Traxel et al. | |
| 6,725,080 B2 | 4/2004 | Melkent et al. | |
| 6,725,082 B2 | 4/2004 | Sati et al. | |
| 6,752,812 B1 | 6/2004 | Truwit | |
| 6,796,988 B2 | 9/2004 | Melkent et al. | |
| 6,887,245 B2 | 5/2005 | Kienzle et al. | |

(Continued)

*Primary Examiner* — Eduardo C Robert
*Assistant Examiner* — Julianna N Harvey
(74) *Attorney, Agent, or Firm* — Sorell, Lenna & Schmidt, LLP

(57) ABSTRACT

A surgical instrument comprises a first member including an inner surface that defines a cavity and an outer surface configured to space tissue. The first member includes a first locking surface. A second member is configured for disposal within the cavity and extends between a first end configured to penetrate tissue and a second end configured to generate a signal representative of a position of the second member. The second member includes a second locking surface. The members are disposable between a first orientation such that the locking surfaces are engaged to resist relative axial translation of the members and a second orientation such that the locking surfaces are disengaged and the second member is axially translatable relative to the first member. Systems and methods are disclosed.

3 Claims, 21 Drawing Sheets

(56) References Cited

U.S. PATENT DOCUMENTS

| | | |
|---|---|---|
| 6,902,569 B2 | 6/2005 | Parmer et al. |
| 6,932,823 B2 | 8/2005 | Grimm et al. |
| 6,996,487 B2 | 2/2006 | Jutras et al. |
| 7,008,430 B2 | 3/2006 | Dong et al. |
| 7,063,705 B2 | 6/2006 | Young et al. |
| 7,072,707 B2 | 7/2006 | Galloway et al. |
| 7,130,676 B2 | 10/2006 | Barrick et al. |
| 7,166,114 B2 | 1/2007 | Moctezuma De La Barrera et al. |
| 7,194,295 B2 | 3/2007 | Vilsmeier |
| 7,204,840 B2 | 4/2007 | Skakoon et al. |
| 7,213,598 B2 | 5/2007 | Zeiss et al. |
| 7,217,276 B2 | 5/2007 | Henderson et al. |
| 7,226,456 B2 | 6/2007 | O'Neil et al. |
| 7,235,084 B2 | 6/2007 | Skakoon et al. |
| 7,237,556 B2 | 7/2007 | Smothers et al. |
| 7,274,958 B2 | 9/2007 | Jutras et al. |
| 7,277,594 B2 | 10/2007 | Hofstetter et al. |
| 7,327,306 B2 | 2/2008 | Laroche |
| 7,346,417 B2 | 3/2008 | Luth et al. |
| 7,383,073 B1 | 6/2008 | Abovitz et al. |
| 7,458,977 B2 | 12/2008 | McGinley et al. |
| 7,477,926 B2 | 1/2009 | McCombs |
| 7,497,863 B2 | 3/2009 | Solar et al. |
| 7,547,307 B2 | 6/2009 | Carson et al. |
| 7,559,935 B2 | 7/2009 | Solar et al. |
| 7,612,708 B2 | 11/2009 | Laroche |
| 7,623,250 B2 | 11/2009 | Moctezuma de la Barrera et al. |
| 7,636,596 B2 | 12/2009 | Solar |
| 7,637,915 B2 | 12/2009 | Parmer et al. |
| 7,641,660 B2 | 1/2010 | Lakin et al. |
| 7,643,862 B2 | 1/2010 | Schoenefeld |
| 7,658,879 B2 | 2/2010 | Solar |
| 7,668,584 B2 | 2/2010 | Jansen et al. |
| 7,699,854 B2 | 4/2010 | Mazzocchi et al. |
| 7,704,260 B2 | 4/2010 | Skakoon et al. |
| 7,744,606 B2 | 6/2010 | Miller et al. |
| 7,747,306 B2 | 6/2010 | Nycz et al. |
| 7,749,223 B2 | 7/2010 | Lavigna et al. |
| 7,751,865 B2 | 7/2010 | Jascob et al. |
| 7,764,985 B2 | 7/2010 | McCombs et al. |
| 7,771,436 B2 | 8/2010 | Moctezuma De La Barrera et al. |
| 7,776,055 B2 | 8/2010 | Kienzle, III et al. |
| 7,794,467 B2 | 9/2010 | McGinley et al. |
| 7,803,163 B2 | 9/2010 | Skakoon |
| 7,815,651 B2 | 10/2010 | Skakoon et al. |
| 7,818,044 B2 | 10/2010 | Dukesherer et al. |
| 7,828,809 B2 | 11/2010 | Skakoon et al. |
| 7,833,231 B2 | 11/2010 | Skakoon et al. |
| 7,840,253 B2 | 11/2010 | Tremblay et al. |
| 7,840,256 B2 | 11/2010 | Lakin et al. |
| 7,857,820 B2 | 12/2010 | Skakoon et al. |
| 7,857,821 B2 | 12/2010 | Couture et al. |
| 7,862,568 B2 | 1/2011 | Vilsmeier et al. |
| 7,862,570 B2 | 1/2011 | Russell et al. |
| 7,867,242 B2 | 1/2011 | Solar et al. |
| 7,873,400 B2 | 1/2011 | Moctezuma De La Barrera et al. |
| 7,877,890 B2 | 2/2011 | Weber |
| 7,879,040 B2 | 2/2011 | Bharadwaj |
| 7,881,770 B2 | 2/2011 | Melkent et al. |
| 7,896,889 B2 | 3/2011 | Mazzocchi et al. |
| 7,933,640 B2 | 4/2011 | Kienzle, III et al. |
| 7,967,764 B2 | 6/2011 | Lidgren et al. |
| 7,971,341 B2 | 7/2011 | Dukesherer et al. |
| 7,981,120 B2 | 7/2011 | Mazzocchi et al. |
| 7,987,001 B2 | 7/2011 | Teichman et al. |
| 8,057,407 B2 | 11/2011 | Martinelli et al. |
| 8,083,795 B2 | 12/2011 | Lange et al. |
| 8,105,339 B2 | 1/2012 | Melkent et al. |
| 8,109,942 B2 | 2/2012 | Carson |
| 8,116,850 B2 | 2/2012 | Solar |
| 8,126,533 B2 | 2/2012 | Lavallee |
| 8,177,788 B2 | 5/2012 | McLean et al. |
| 8,192,445 B2 | 6/2012 | Parmer et al. |
| 8,214,016 B2 | 7/2012 | Lavallee et al. |
| 8,239,001 B2 | 8/2012 | Verard et al. |
| 2006/0184174 A1* | 8/2006 | Harris et al. .............. 606/80 |
| 2008/0119857 A1* | 5/2008 | Potash et al. ............. 606/72 |

* cited by examiner

SURGICAL IMPLANT SYSTEM AND METHOD

TECHNICAL FIELD

The present disclosure generally relates to medical devices for the treatment of musculoskeletal disorders, and more particularly to a surgical system for creating a surgical pathway and/or preparing a surgical site, and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments, such as, for example, wires and cannulated instrumentation can be employed to establish passageways for delivery of the implants. This disclosure describes an improvement over these prior art technologies.

SUMMARY

In one embodiment, in accordance with the principles of the present disclosure, a surgical instrument is provided. The surgical instrument comprises a first member including an inner surface that defines a cavity and an outer surface being configured to space tissue. The first member further includes a first locking surface. A second member is configured for disposal within the cavity and extends between a first end configured to penetrate tissue and a second end configured to generate a signal representative of a position of the second member. The second member includes a second locking surface. The members are disposable between a first orientation such that the locking surfaces are engaged to resist relative axial translation of the members and a second orientation such that the locking surfaces are disengaged and the second member is axially translatable relative to the first member.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
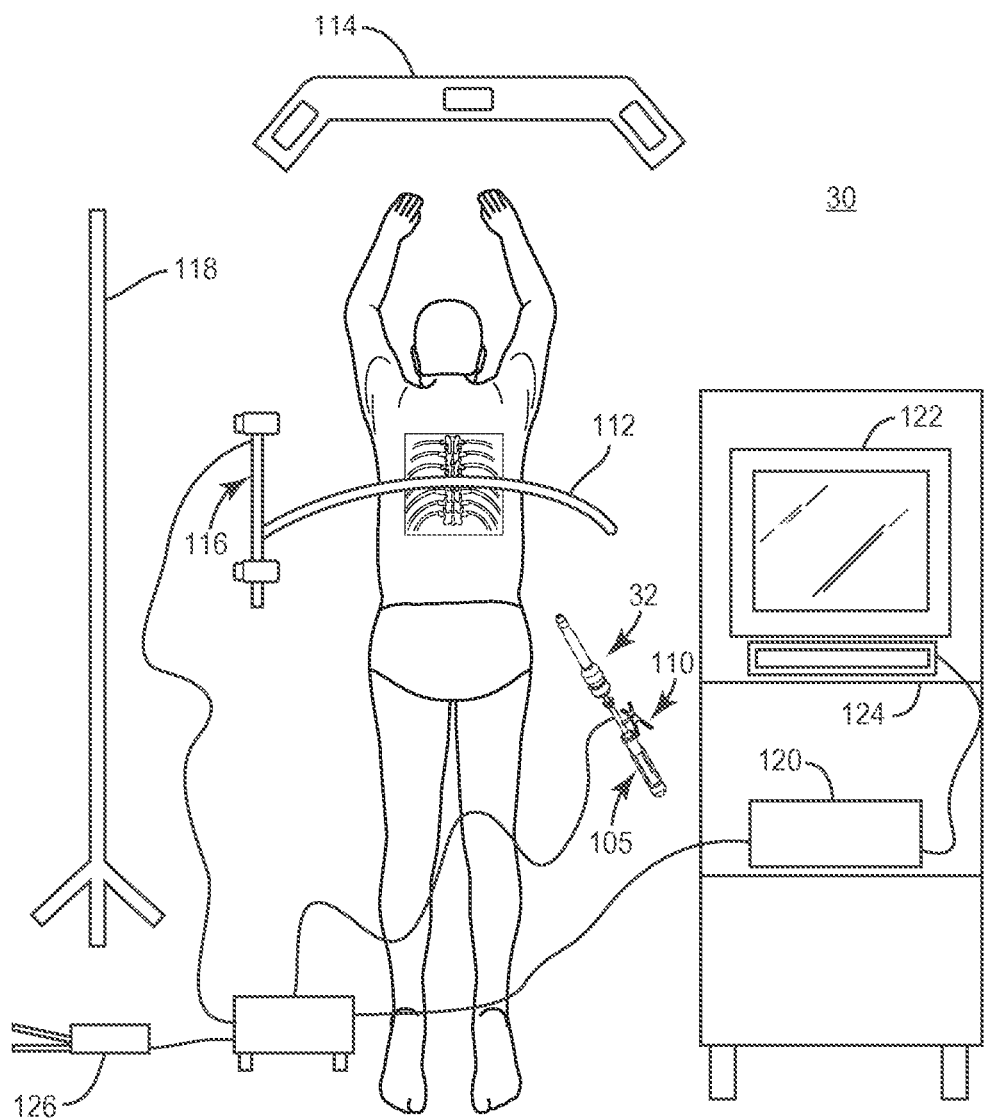
FIG. 1 is a plan view of one embodiment of a surgical implant system in accordance with the principles of the present disclosure.
Figure 2:
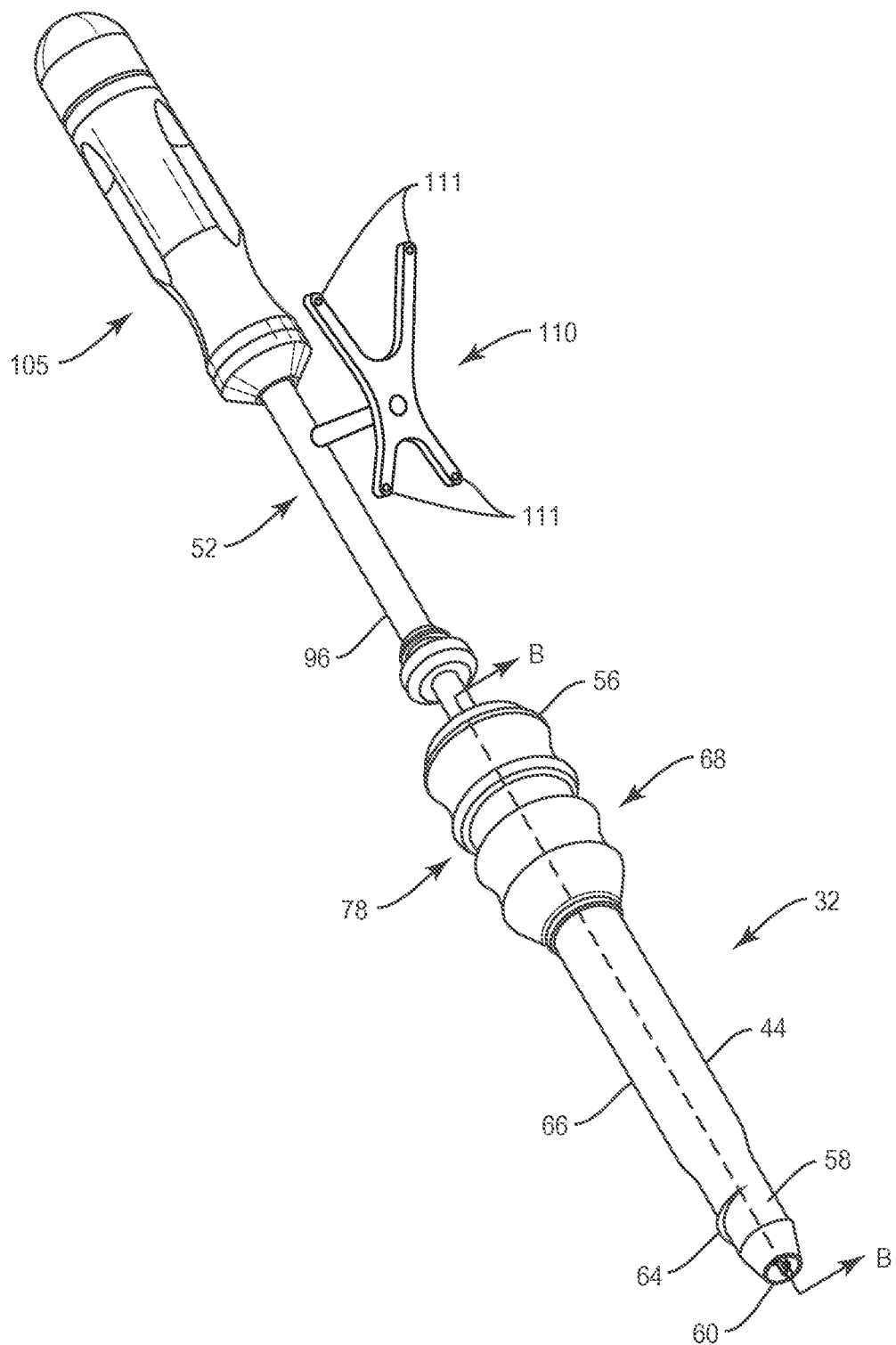
FIG. 2 is a perspective view of components of the system shown in FIG. 1.
Figure 3:
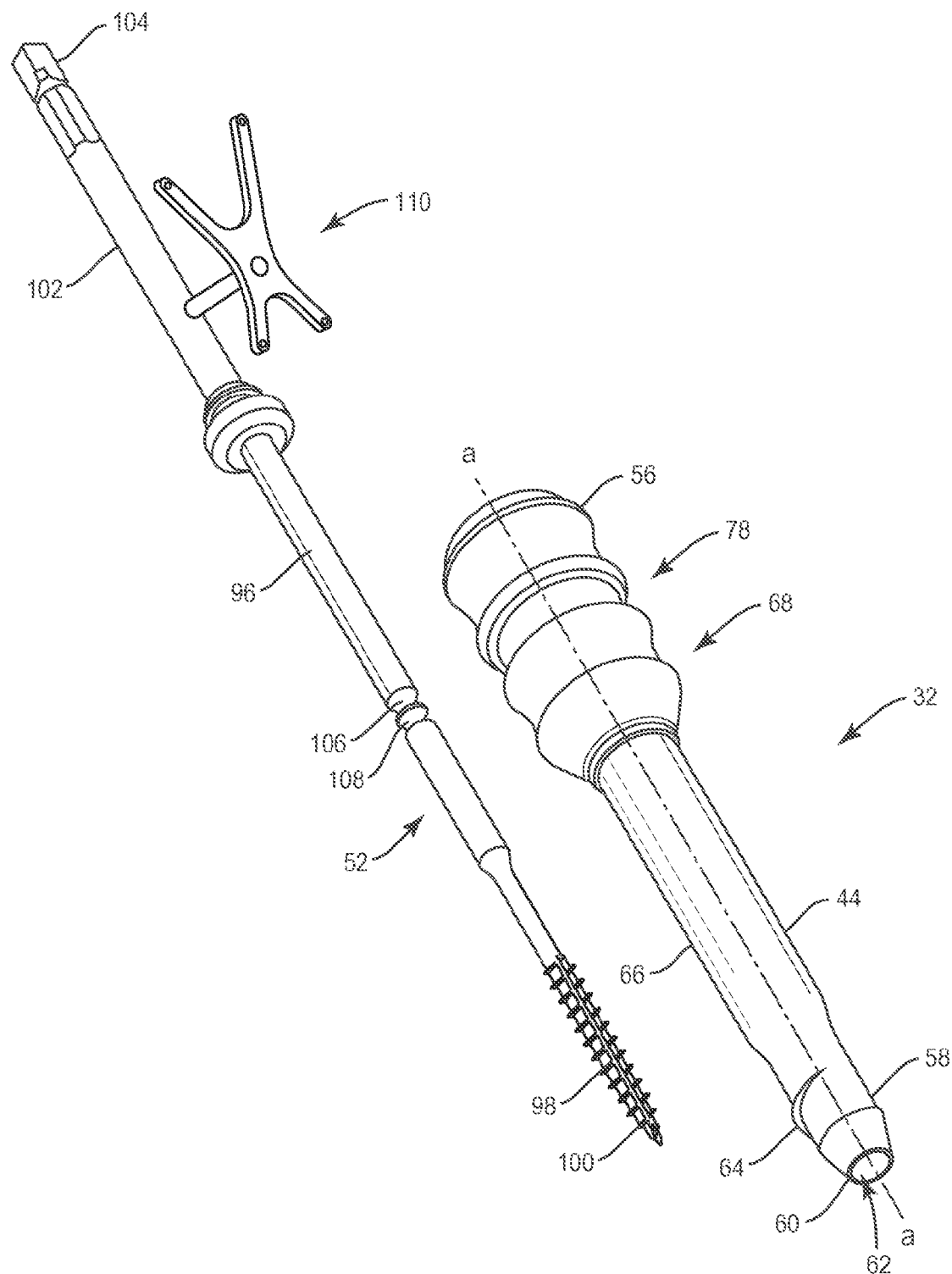
FIG. 3 is a perspective view of components of the system shown in FIG. 1 with parts separated.
Figure 4:
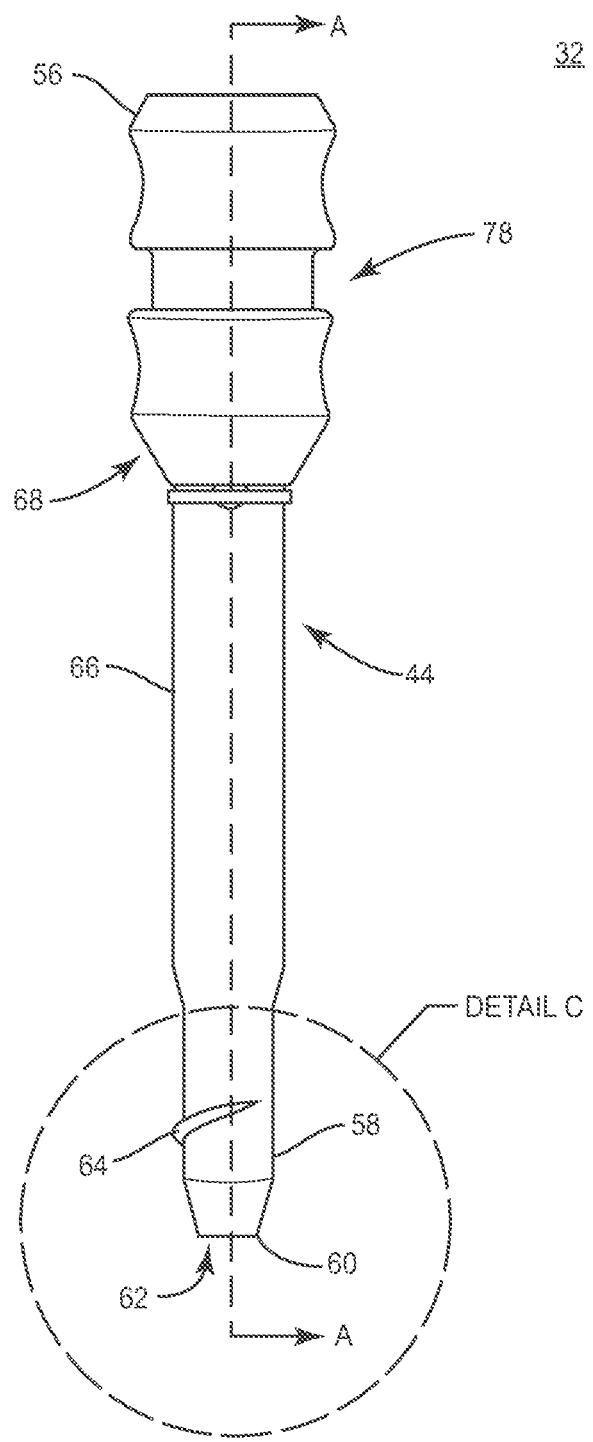
FIG. 4 is a side view of components of the system shown in FIG. 1.

The exemplary embodiments of a surgical system are discussed in terms of medical devices for the treatment of musculoskeletal disorders and more particularly, in terms of a surgical implant system for creating a surgical pathway and/or preparing a surgical site, and a method for treating a spine.

In one embodiment, the system includes a surgical instrument that includes a tap and dilator assembly having navigation to guide and/or insert the tap with a surgical site without x-ray fluoroscopy. In one embodiment, the system includes a tap having one or a plurality of grooves, such as, for example, radial grooves, configured to receive a portion of a tissue protector, such as, for example, a dilator to prevent movement of the tap relative to the dilator. In one embodiment, an outer surface of the dilator includes a thread configured to engage fascia to hold the dilator in place within the anatomy of a patient.

In one embodiment, the system includes a surgical instrument having a set of taps and tissue protectors that utilize navigation to insert percutaneous pedicle screws without the use of guidewires. In some embodiments, the system may be employed with other minimally invasive and/or open surgical procedures. This configuration reduces fluoroscopy exposure. In one embodiment, the tap can be oriented flush with a tissue protector at the surgical site. In one embodiment, the tap can be oriented in an initial orientation to extend 5 millimeters (mm) from a distal end of a tissue protector at the surgical site. In one embodiment, the tap can be oriented in an initial orientation to extend 10 mm from a distal end of a tissue protector at the surgical site. In one embodiment, the tap can be oriented to extend 50 mm from a distal end of a tissue protector to penetrate tissue at the surgical site. In one embodiment, the system includes a surgical instrument that can be oriented between a locked position and an unlocked position.

In one embodiment, the system is employed with a method that includes the steps of selecting a flush or 10 mm out position for the tap relative to the tissue protector; determining a selected trajectory for the tap using navigation; orienting the instrument from a locked position to an unlocked position; hammering a distal end of the tap into tissue; and tapping into the tissue. In one embodiment, the surgical instrument is manipulated for an initial 10 mm of tapping and then released. In one embodiment, the surgical instrument is manipulated for an initial 5 mm of tapping and then released. In one embodiment, the step of selecting includes a flush or 5 mm out position for the tap relative to the tissue protector.

In one embodiment, the system includes a surgical instrument having a sliding locking collar. In one embodiment, the system includes a surgical instrument having a fascia thread disposed at a distal end of a tissue protector, such as, for example, a tissue dilator, for holding the dilator in place. In one embodiment, the system includes a surgical instrument having a lock that includes spring tabs, which move away from and towards a central axis to lock and unlock the tap. In one embodiment, a sliding collar holds the spring tabs in a locked position or allows them to spring away from the central axis to the unlocked position.

In some embodiments, one or all of the components of the system may be disposable, peel pack and/or pre packed sterile devices. One or all of the components of the system may be reusable. The system may be configured as a kit with multiple sized and configured components.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure.

It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-17, there are illustrated components of a surgical implant system 30, in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference. The components of system 30, individually or collectively, may also be fabricated from a heterogeneous material such as a combination of two or more of the above-described materials. The components of system 30 may be monolithically formed, integrally connected or include fastening elements and/or instruments, as described herein.

System 30 is employed, for example, with an open or mini-open, minimal access and/or minimally invasive including percutaneous surgical technique to create a cavity for an implant, such as, for example, a bone fastener at a surgical site within a body of a patient, for example, a section of a spine. In one embodiment, the components of system 30 are configured to create a cavity in vertebrae to fix a spinal rod, connector and/or plate to a spine via a bone fastener for a surgical treatment to treat various spine pathologies, such as those described herein.

Figure 5:
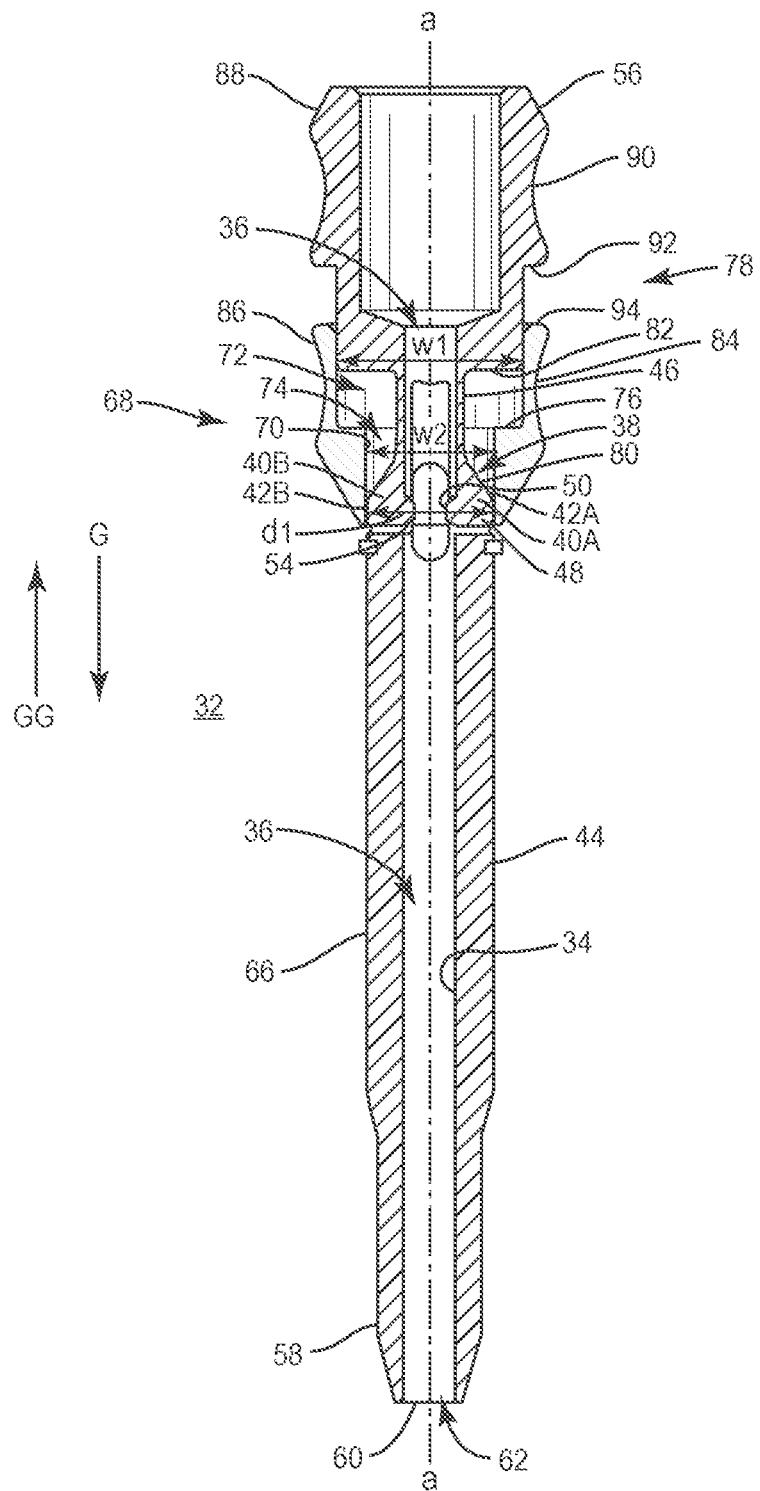
FIG. 5 is a cross section view of the components shown in FIG. 4 taken along lines A-A.
Figure 11:
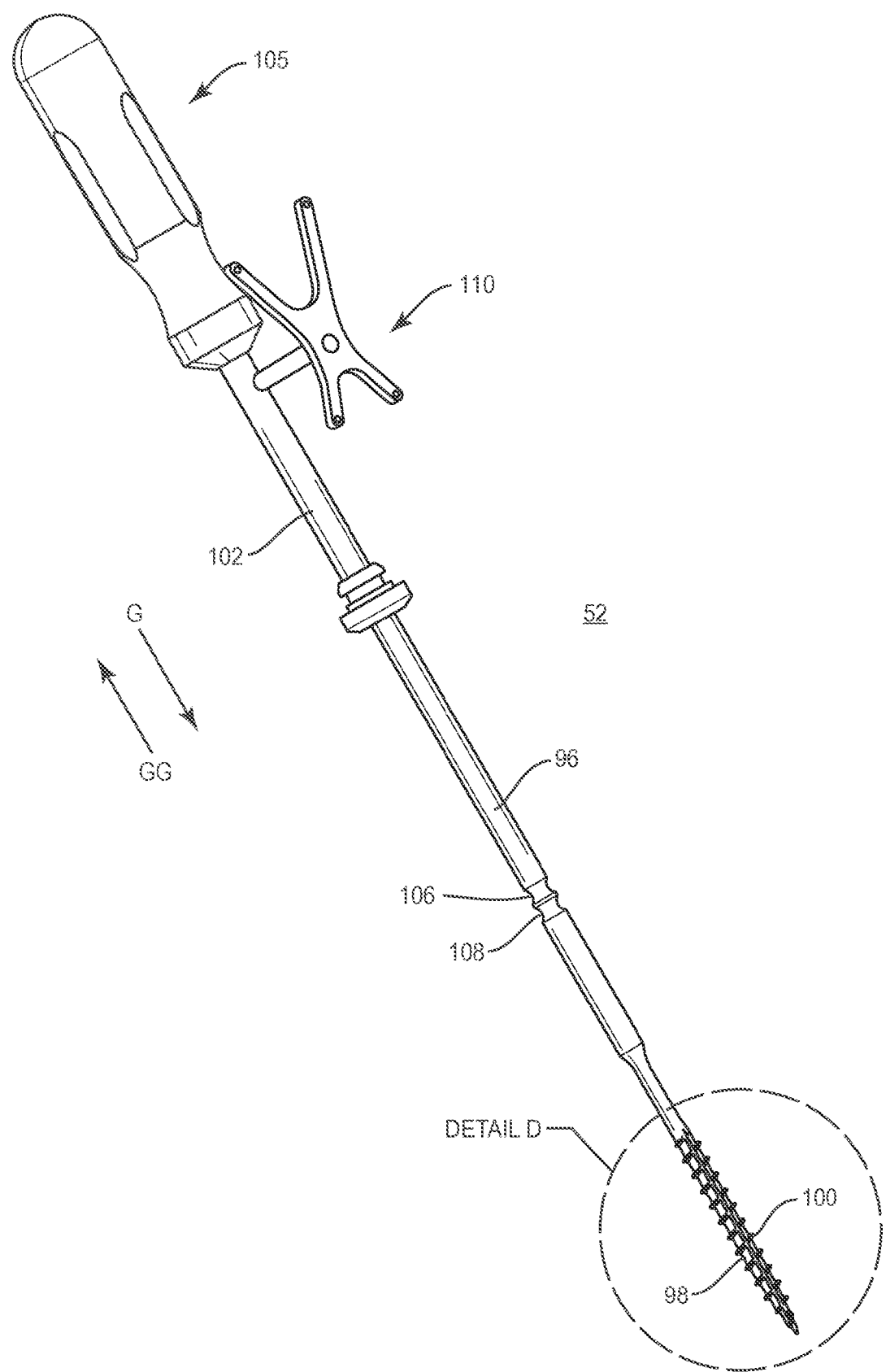
FIG. 11 is a side view of component of the system shown in FIG. 1.
Figure 12:
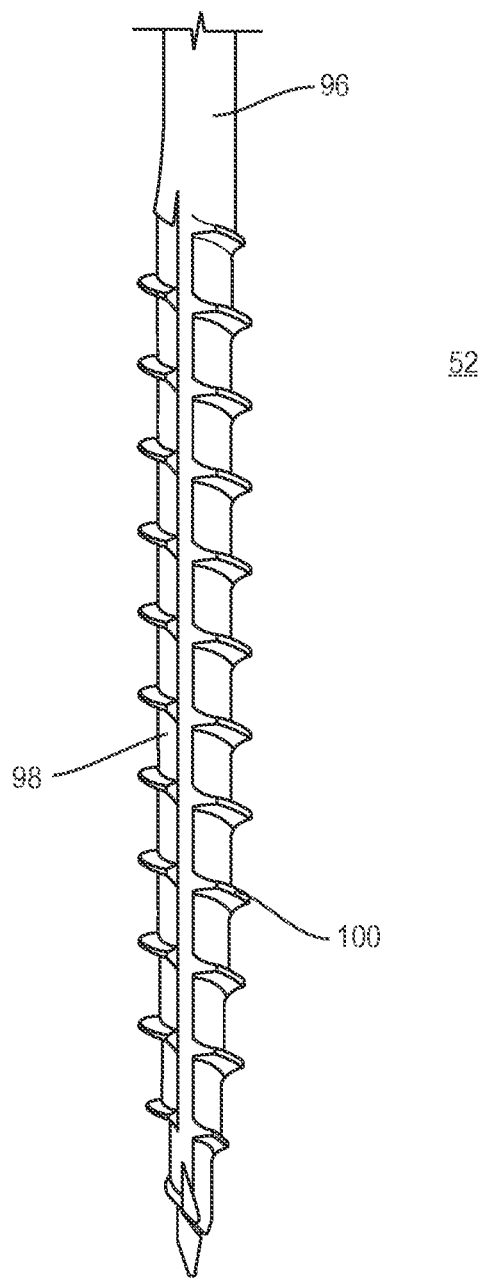
FIG. 12 is an enlarged perspective view of detail D shown in FIG. 11.

System 30 comprises a surgical instrument that includes a first member, such as, for example, a tissue dilator 32, as shown in FIG. 5, extending along an axis a having an inner surface 34 that defines a cavity, such as, for example, an axial passageway 36 and a locking surface 38, which includes tabs 40A, 40B described below, that are transversely movable relative to surface 34. Passageway 36 has a cylindrical cross sectional configuration adapted for movable disposal of a second member, such as, for example, a tap 52 (FIG. 11). In some embodiments, passageway 36 may have alternate cross section configurations, such as, for example, oval, oblong, triangular, square, hexagonal, polygonal, irregular, uniform, non-uniform and/or tapered. In some embodiments, passageway 36 may be disposed at alternate orientations relative to axis a, such as, for example, transverse, perpendicular and/or other angular orientations such as acute or obtuse, according to the requirements of a particular application.

Surface 38 includes a movable tab 40A and a movable tab 40B. Tab 40A is disposed in substantial alignment with a thickness of dilator 32 such that an outer surface 42A of tab 40A is substantially aligned with an outer surface 44 of dilator 32. Tab 40B is disposed in substantial alignment with a thickness of dilator 32 such that an outer surface 42B of tab 40B is substantially aligned with outer surface 44 of dilator 32. In some embodiments, dilator 32 may include one or a plurality of tabs. Tabs 40A, 40B are disposed circumferentially about surface 44. In one embodiment, dilator 32 includes a pair of tabs disposed opposite one another such that an inner surface of one tab faces an inner surface of the other tab. In one embodiment, tabs 40A, 40B are resiliently biased outwardly in a direction opposite surface 34. In one embodiment, tabs 40A, 40B each extend from surface 34 in a cantilevered configuration.

Each of tabs 40A, 40B includes a first portion 46 having a first thickness and a second portion 48 having a second thickness that is greater than the first thickness. Portion 48 includes a flange 50 projecting from surface 38 configured for disposal in tap 52, as will be discussed. Flange 50 extends perpendicular to axis a. In one embodiment, flange 50 includes a bevel 54 at an end of flange 50 opposite surface 34 to facilitate insertion of flange into a portion of tap 52, as will be discussed. In some embodiments, flange 50 may be disposed at alternate orientations relative to axis a, such as, for example, transverse and/or other angular orientations, such as, acute or obtuse, according to the requirements of a particular application. In some embodiments, all or only a portion of bevel 54 may have various surface configurations, such as, for example, rough, arcuate, undulating, porous, semi-porous, dimpled, polished and/or textured, to enhance engagement of flange 50 with tap 52. In some embodiments, bevel 54 may be variously configured and dimensioned, such as, for example, planar, concave, convex, polygonal, irregular, uniform, non-uniform, staggered, tapered, consistent or variable, depending on the requirements of a particular application.

Dilator 32 extends along axis a between a first end 56 and a second end 58 including a planar distal face 60 extending perpendicular to axis a and a circular opening 62 extending through face 60 that is in communication with passageway 36. In some embodiments, face 60 may be variously configured and dimensioned, such as, for example, concave, convex, polygonal, irregular, uniform, non-uniform, staggered, tapered, consistent or variable, depending on the requirements of a particular application. In some embodiments, opening 62 may have alternate cross section configurations, such as, for example, oval, oblong, triangular, square, hexagonal, polygonal, irregular, uniform, non-uniform and/or tapered.

End 58 extends in a tapered configuration to face 60. Surface 44 is configured to space apart tissue and is smooth or even to prevent injury to the anatomy of a patient, such as, for example, soft tissue, when dilator 32 is inserted through an incision and delivered to the surgical site. Dilator 32 includes an intermediate portion 66 between ends 56, 58. Dilator 32 is tapered between portion 66 and end 58. Surface 44 includes a threaded portion 64 (FIG. 4) adjacent end 58 configured for fixation with tissue, such as, for example, fascia. In some embodiments, all or a portion of dilator 32 may be variously configured and dimensioned, such as, for example, planar, concave, convex, polygonal, irregular, uniform, non-uniform, staggered, tapered, consistent or variable, depending on the requirements of a particular application. In some embodiments, all or only a portion of surface 44 may have various surface configurations, such as, for example, rough, threaded, arcuate, undulating, porous, semi-porous, dimpled, polished and/or textured, to enhance fixation of dilator 32 with tissue.

Dilator 32 includes a movable collar 68 having an inner surface 70 extending parallel to axis a and defining a proximal portion 72 having a width w1 and a distal portion 74 having a width w2 that is less than width w1. Collar 68 includes a ledge 76 between portions 72, 74 extending perpendicular to axis a. Portion 72 is configured for movable disposal of a handle portion 78 positioned at end 56. In some embodiments, surface 70 and/or ledge 76 may be disposed at alternate orientations, relative to axis a, such as, for example, transverse, perpendicular and/or other angular orientations such as acute or obtuse, coaxial and/or may be offset or staggered, according to the requirements of a particular application.

Figure 6:
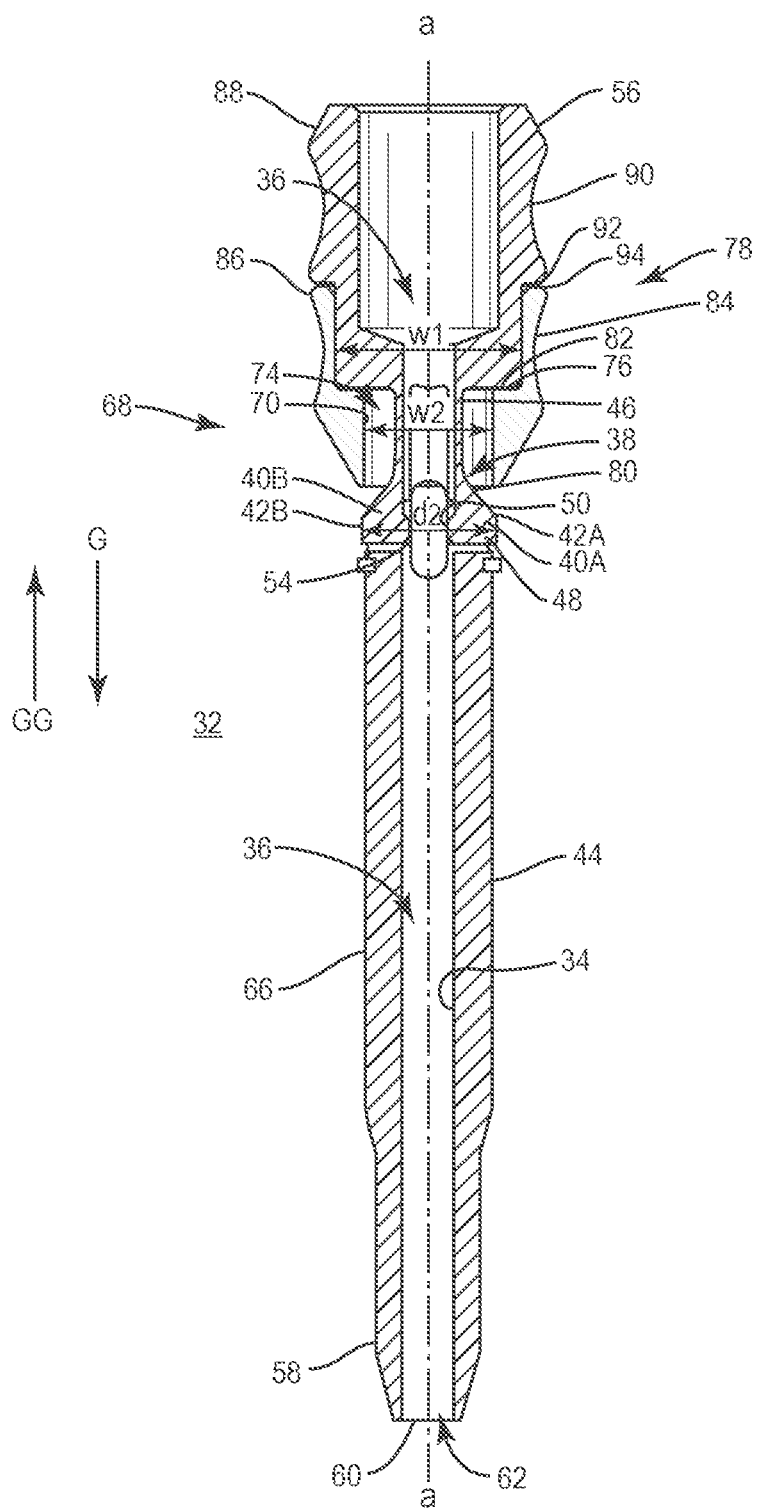
FIG. 6 is a cross section view of the components shown in FIG. 4 taken along lines A-A.

Surface 70 is engageable with surface 38 along portion 74 to move tabs 40A, 40B into engagement with tap 52. Tabs 40A, 40B are resiliently biased outwardly such that there is a distance d2 between surfaces 42A, 42B, as shown in FIG. 6. Distance d2 is greater than width w2. Moving collar 68, in the direction shown by arrow G, relative to tabs 40A, 40B causes surface 70 to engage surfaces 42A, 42B such that there is a distance d1 between surfaces 42A, 42B, as shown in FIG. 5. Tabs 40A, 40B include a tapered portion between portion 48 and portion 46 defining a ramp 80. As collar 68 moves, in the direction shown by arrow G, surface 70 translates along ramp 80 to move tabs 40A, 40B such that surfaces 42A, 42B engage surface 70 adjacent portion 48, as shown in FIG. 5. When dilator 32 is disposed in a configuration, as shown in FIG. 5, a distal face 82 of portion 78 is spaced apart from ledge 76. When dilator 32 is disposed in a configuration, as shown in FIG. 6, face 82 engages ledge 76.

Collar 68 includes a smooth or even outer surface 84 that is tapered between a proximal end of collar 68 and a distal end of collar 68. Surface 84 includes a circumferential indent 86 extending perpendicular to axis a into surface 84. Indent 86 is convexly curved to facilitate gripping by a medical practitioner. In some embodiments, indent 86 may be variously configured and dimensioned, such as, for example, planar, concave, convex, polygonal, irregular, uniform, non-uniform, staggered, tapered, consistent or variable, depending on the requirements of a particular application. In some embodiments, indent 86 may be disposed at alternate orientations, relative to axis a, such as, for example, transverse, perpendicular and/or other angular orientations such as acute or obtuse, coaxial and/or may be offset or staggered, according to the requirements of a particular application.

Portion 78 includes a smooth or even outer surface 88 including a circumferential indent 90 extending perpendicular to axis a into surface 88. Indent 90 is convexly curved to facilitate gripping by a medical practitioner. Surface 88 defines an interface 92 between a proximal end of portion 78 and a distal end of portion 78 extending transverse to axis a. Interface 92 engages a proximal face 94 of collar 68 when face 82 engages ledge 76, as shown in FIG. 6. In some embodiments, indent 90 may be variously configured and dimensioned, such as, for example, planar, concave, convex, polygonal, irregular, uniform, non-uniform, staggered, tapered, consistent or variable, depending on the requirements of a particular application. In some embodiments, indent 90 and/or interface 92 may be disposed at alternate orientations, relative to axis a, such as, for example, transverse, perpendicular and/or other angular orientations such as acute or obtuse, coaxial and/or may be offset or staggered, according to the requirements of a particular application.

Tap 52 is configured for movable disposal within passageway 36 such that dilator 32 and tap 52 are coaxial and tap 52 can simultaneously rotate and translate axially within passageway 36. Tap 52 includes a cylindrical shaft 96 having a first end 98 including a screw tap 100 including an external or male thread configured to form an internal or female thread in the tissue such that an implant, such as, for example, a bone fastener, can be threaded into the internal thread formed by tap 52. In one embodiment, screw tap 100 includes a tapered thread to facilitate insertion of screw tap 100 into tissue. In one embodiment, screw tap 100 includes a self-starting thread. In some embodiments, all or a portion of shaft 96 may have alternate cross section configurations, such as, for example, oval, oblong, triangular, square, hexagonal, polygonal, irregular, uniform, non-uniform and/or tapered.

Shaft 96 includes a second end 102 including a drive portion 104 configured to rotate tap 52, in the direction shown by arrow G and/or the direction shown by arrow GG. In some embodiments, portion 104 may be configured to engage an actuator, such as, for example, a surgical instrument, powered drill, hand drill, driver or other tool to rotate tap 52, in the direction shown by arrow G and/or the direction shown by arrow GG. In one embodiment, portion 104 has a hexagonal cross sectional configuration and is configured to engage a correspondingly shaped portion of the actuator. In some embodiments, portion 104 may include a square, triangular, polygonal, star or hexalobe cross sectional configuration configured engage a correspondingly shaped portion of the actuator. In one embodiment, end 102 includes an interchangeable driving handle 105 removably connected to shaft 96 such that torque applied manually or by motorized means to handle 105 is transmitted to shaft 96.

Tap 52 includes a second locking surface, such as, for example, radial grooves 106, 108 formed in shaft 96 each extending transverse to axis a. In some embodiments, tap 52 may include a plurality of grooves 106, 108 disposed at various locations along shaft 96 to vary the position of screw tap 100 relative to face 60. Grooves 106, 108 are axially spaced apart from one another and are positioned between ends 98, 102. Grooves 106, 108 each have a concave shape when viewed from a direction that is transverse to axis a. In some embodiments, groove 106 and/or groove 108 may be disposed at alternate orientations, relative to axis a, such as, for example, transverse, perpendicular and/or other angular orientations such as acute or obtuse, coaxial and/or may be offset or staggered, according to the requirements of a particular application. In some embodiments, groove 106 and/or groove 108 may be variously configured and dimensioned, such as, for example, planar, concave, convex, polygonal, irregular, uniform, non-uniform, staggered, tapered, consistent or variable, depending on the requirements of a particular application.

Figure 7:
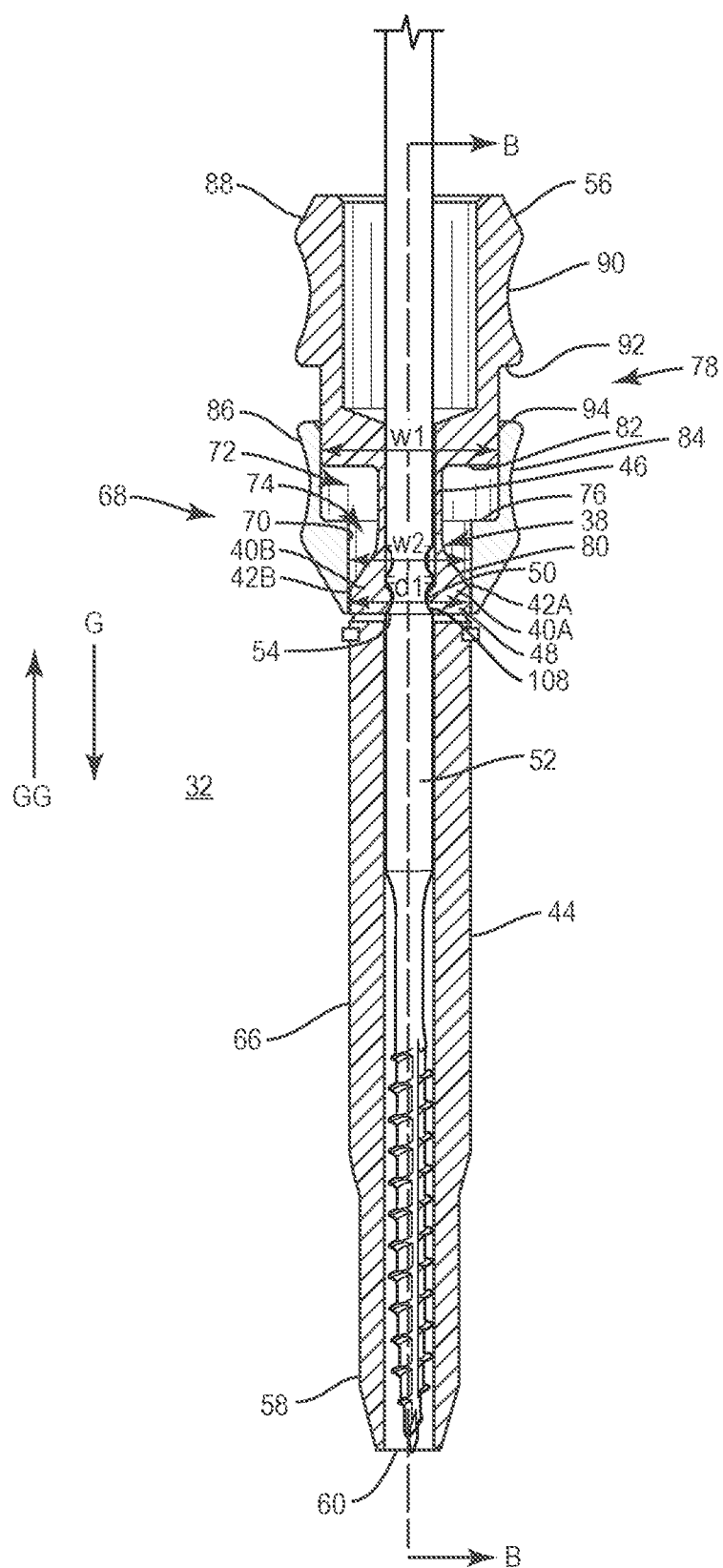
FIG. 7 is a cross section view of components of the system shown in FIG. 2 taken along lines B-B.
Figure 8:
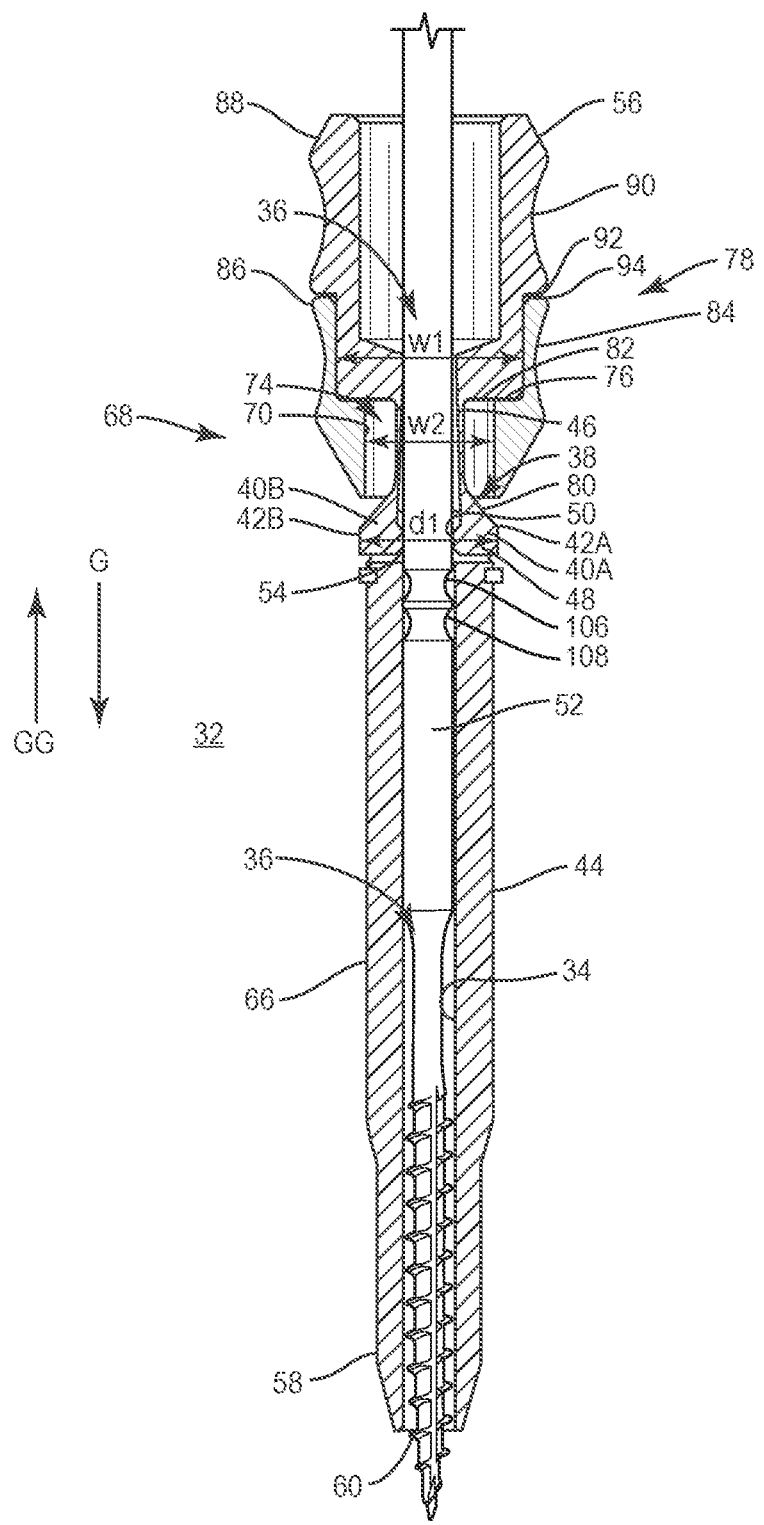
FIG. 8 is a cross section view of components of the system shown in FIG. 2 taken along lines B-B.
Figure 9:
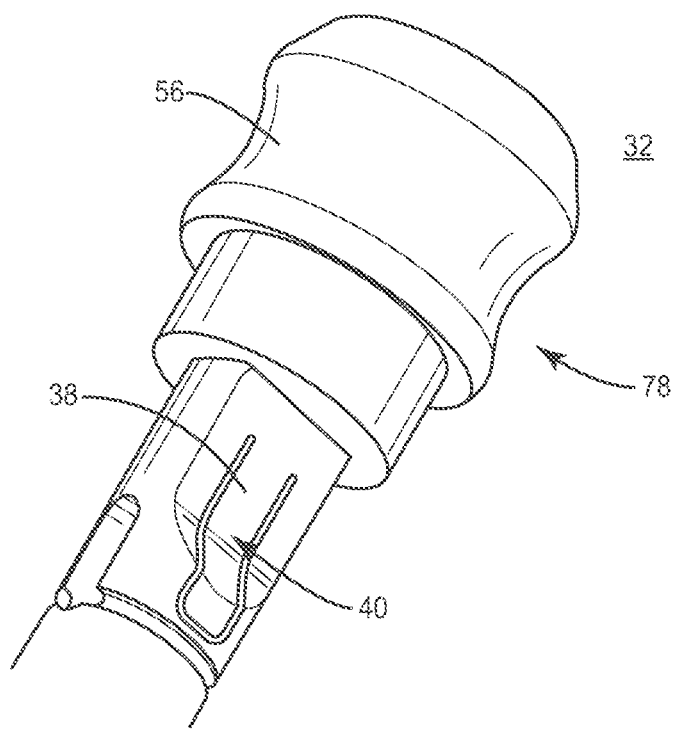
FIG. 9 is a break away view of a component of the system shown in FIG. 2.
Figure 10:
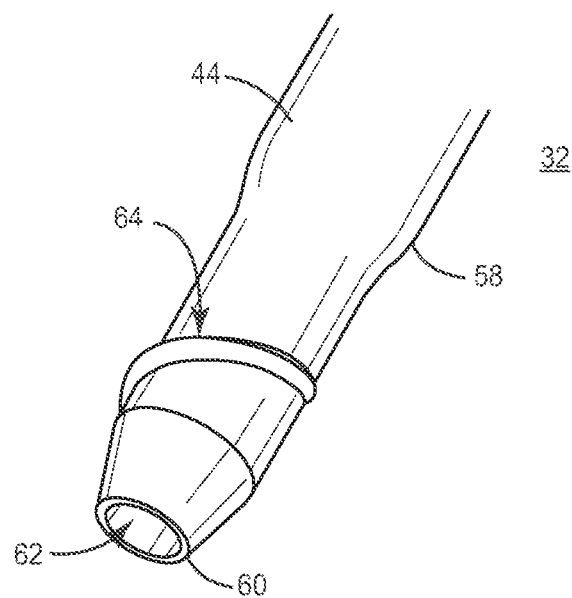
FIG. 10 is an enlarged perspective view of detail C shown in FIG. 4.
Figures 13, 14:
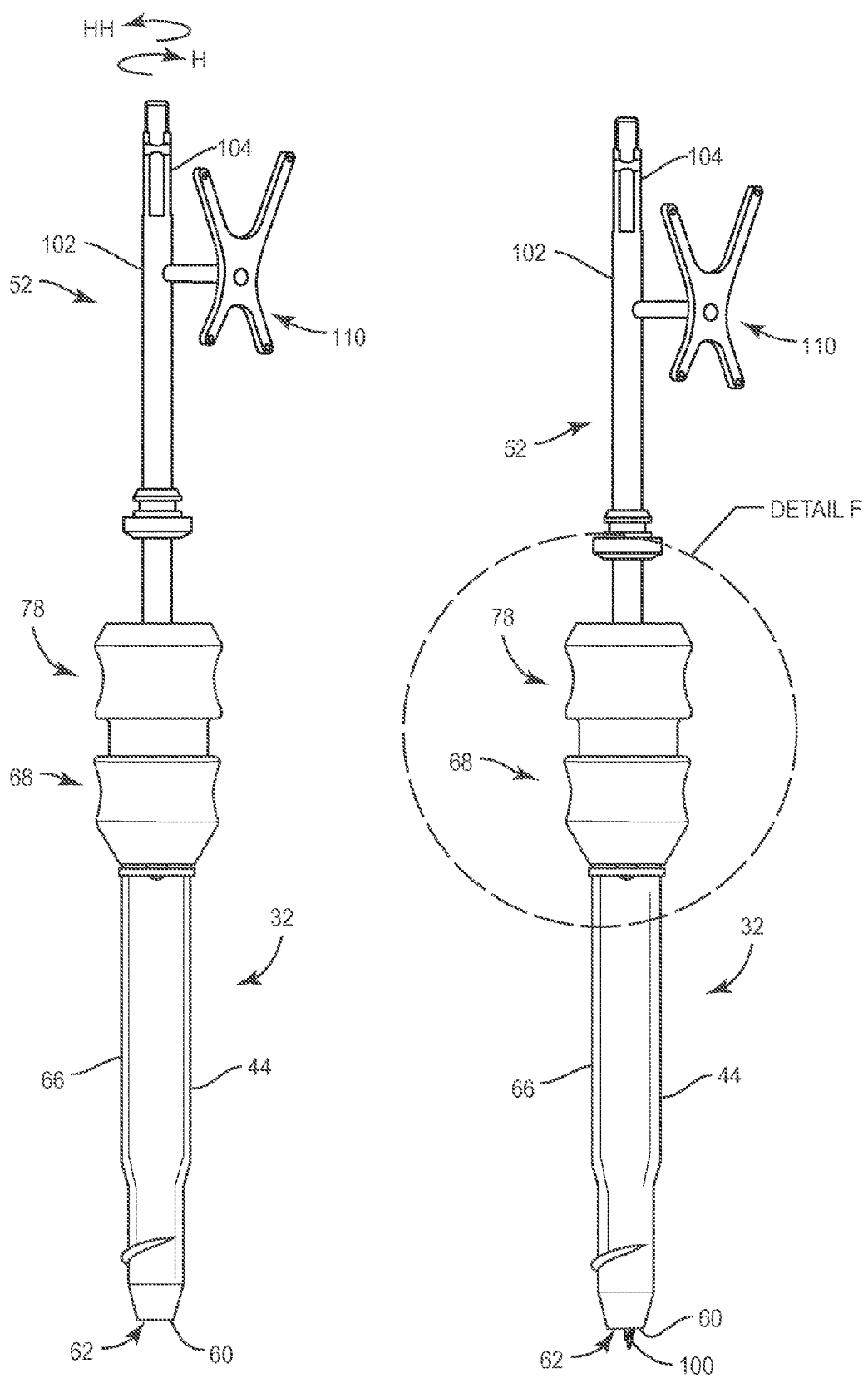
FIG. 13 is a side view of components of the system shown in FIG. 1.
FIG. 14 is a side view of components of the system shown in FIG. 1.
Figure 15:
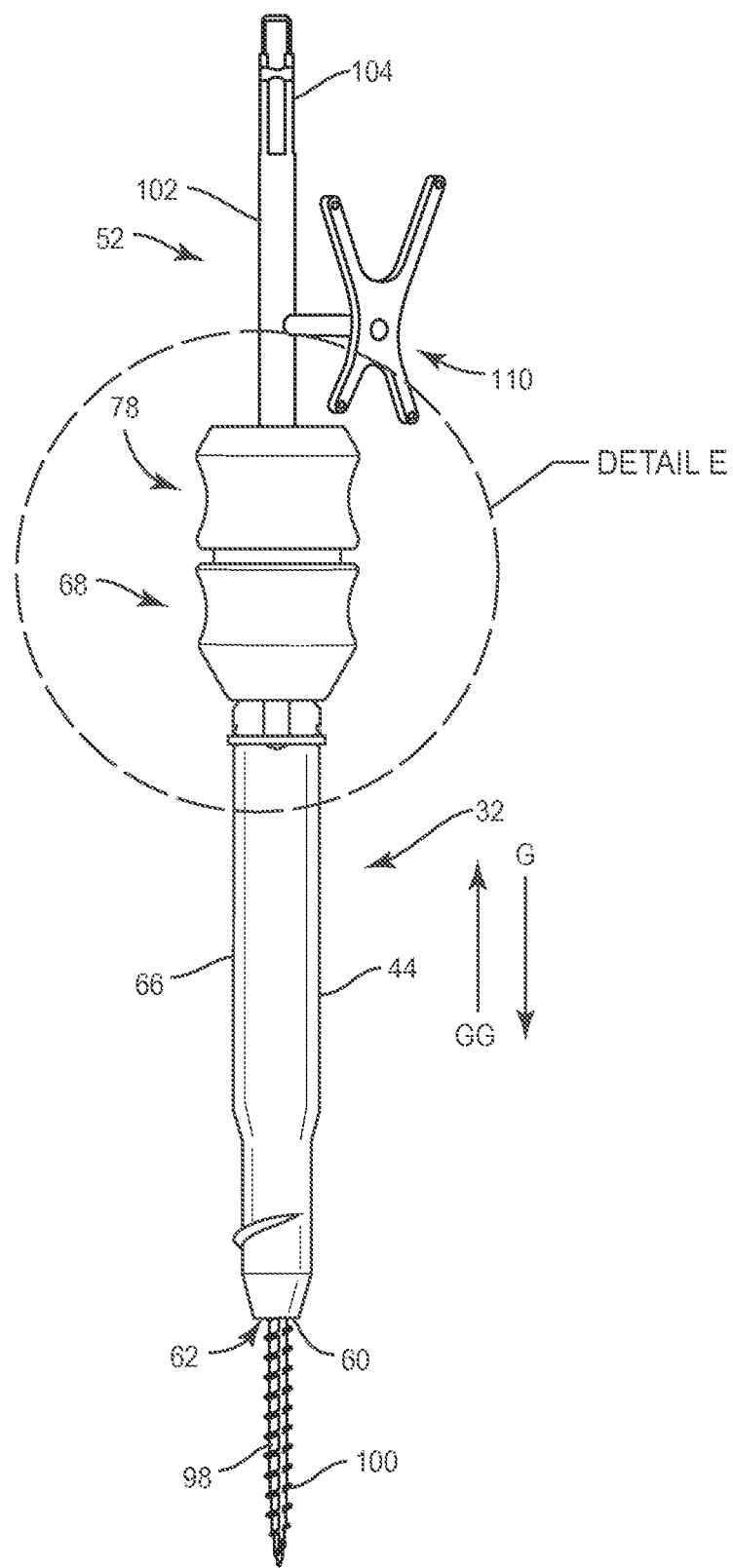
FIG. 15 is a side view of components of the system shown in FIG. 1.
Figure 16:
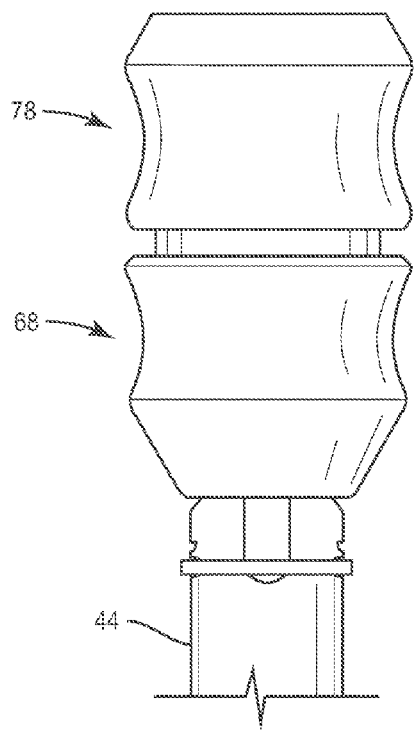
FIG. 16 is an enlarged side view of detail E shown in FIG. 15.
Figure 17:
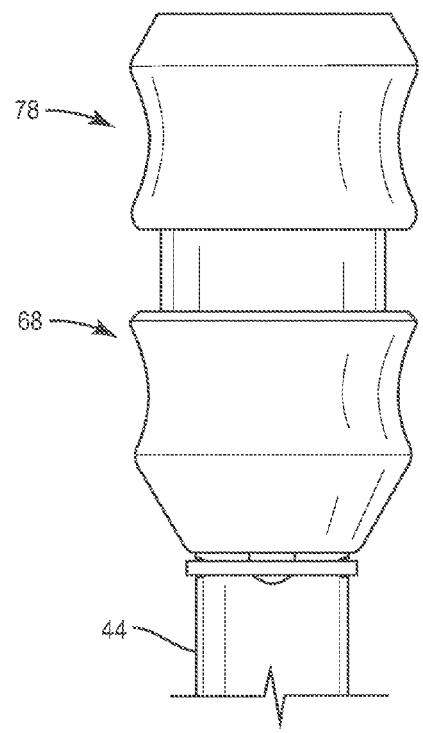
FIG. 17 is an enlarged side view of detail F shown in FIG. 14.

Grooves 106, 108 are configured for disposal of tabs 40A, 40B to prevent axial translation of tap 52 within passageway 36. Tabs 40A, 40B are movable between a locking orientation, in which there is a distance d1 between surfaces 42A, 42B, as shown in FIG. 5 and a non-locking orientation, in which there is a distance d2 between surfaces 42A, 42B, as shown in FIG. 6. Tabs 40A, 40B are movable from the locking orientation to the non-locking orientation by moving collar 68 relative to surface 44, in the direction shown by arrow GG, such that surface 70 is spaced apart from surfaces 42A, 42B thereby allowing tabs 40A, 40B to deflect such that there is a distance d2 between surfaces 42A, 42B. When tabs 40A, 40B are in the non-locking orientation, flanges 50 are spaced apart from grooves 106, 108, as shown in FIG. 8, such that tap 52 is permitted to translate axially relative to dilator 32 within passageway 36. Tabs 40A, 40B are movable from the non-locking orientation to the locking orientation by moving collar 68 relative to surface 44, in the direction shown by arrow G, such that surface 70 engages surfaces 42A, 42B thereby disposing flanges 50 in groove 106 or groove 108, as shown in FIG. 7, to prevent tap 52 from translating axially relative to dilator 32 within passageway 36. Tabs 40A, 40B may engage either groove 106 or groove 108 when tabs 40A, 40B are in the locking orientation such that shaft 96 is selectively disposable in passageway 36 in at least two locking orientations. In the first locking orientation, tabs 40A, 40B are disposed in groove 108 such that a tip of screw tap 100 is disposed within passageway 36 without extending through opening 62, as shown in FIG. 13. In the second locking orientation, tabs 40A, 40B are disposed in groove 106 such that the tip of screw tap 100 extends through opening 62, as shown in FIG. 14. When tabs 40A, 40B are in the non-locking orientation, tap 52 can translate axially within passageway 36, in the direction shown by arrow G, such that screw tap 100 extends beyond face 60, as shown in FIG. 15, or, in the direction shown by arrow GG, such that screw tap 100 does not extend through opening 62, as shown in FIG. 13.

As shown in FIG. 11, tap 52 includes an emitter 110 mounted on an outer surface of shaft 96 between ends 98, 102 configured to generate a signal representative of a position of tap 52. In some embodiments, emitter 110 may include one or a plurality of emitters. In one embodiment, emitter 110 is shaped substantially like the Greek letter pi and comprises four spaced apart emitters 111, for generating a signal representing the trajectory of tap 52 relative to a portion of a patient's anatomy and the depth of screw tap 100 within the patient's anatomy. In one embodiment, emitter 110 includes at least one light emitting diode. In some embodiments, emitter 110 may include other tracking devices capable of being tracked by a corresponding sensor array, such as, for example, a tracking device that actively generates acoustic signals, magnetic signals, electromagnetic signals, radiologic signals. In some embodiments, emitter 110 may be removably attached to tap 52. In some embodiments, emitter 110 may be integrally formed with tap 52 such that tap 52 is a monolithic, unitary body.

As shown in FIG. 1, system 30 includes a tracking device having an emitter array 112 including one or a plurality of emitters that generate signals representing the position of various body reference points of the patient's anatomy. A sensor 114 receives signals from emitter 110 and array 112. In some embodiments, array 112 may be attached to a clamp assembly 116 that is mounted on a support 118 to selectively position array 112 relative to the patient's anatomy, according to the preference of the medical practitioner. Sensor 114 communicates with a processor 120, such as, for example, a digitizer control unit, which processes the signals from emitter 110 and array 112 to provide information regarding the trajectory of tap 52 relative to a portion of the patient's anatomy and the depth of screw tap 100 within the patient's anatomy. Processor 120 sends this information to a monitor 122, which provides a visual representation of the position of screw tap 100 relative to the patient's anatomy to allow the medical practitioner to guide screw tap 100 to a desired location within the patient's anatomy.

Monitor 122 is configured to generate an image from a data set stored in a controller, such as, for example, a computer 124. In some embodiments, the data set may be generated preoperatively using scanning techniques, such as, for example, a CAT scanner or MRI scanner. The image data set includes reference points for at least one body part, such as, for example, the spine of a patient, which have a fixed spatial relation to the body part. Processor 120 is connected to monitor 122, under control of computer 124, and to tap 52.

Sensor 114 is mounted to support 118 and receives and triangulates signals generated by emitter 110 and array 112 to identify the relative position of each of the reference points and tap 52. Processor 120 and computer 124 modify the image data set according to the identified relative position of each of the reference points during the procedure. The position and trajectory of tap 52 provided by emitter 110 and array 112 is processed by processor 120 and computer 124 and is visually displayed against the preoperative image data set stored in computer 124 to provide the medical practitioner with a visual representation of the trajectory of tap 52 relative to a portion of the patient's anatomy and the depth of screw tap 100 within the patient's anatomy. In one embodiment, system 30 includes a foot switch 126 connected to tap 52 and processor 120 for controlling operation of system 30.

Figure 18:
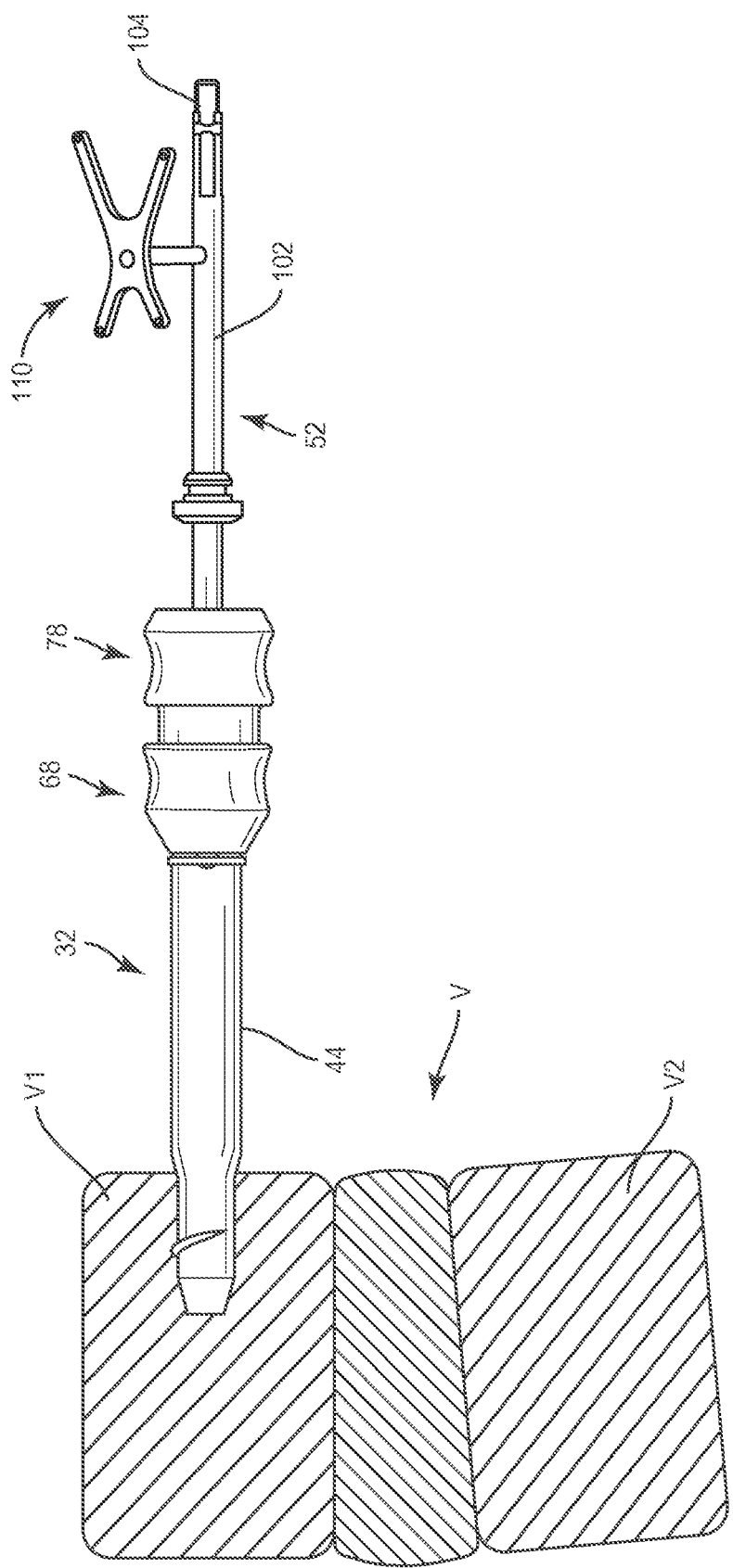
FIG. 18 is a side view of components of the system shown in FIG. 1 disposed with vertebrae.
Figure 19:
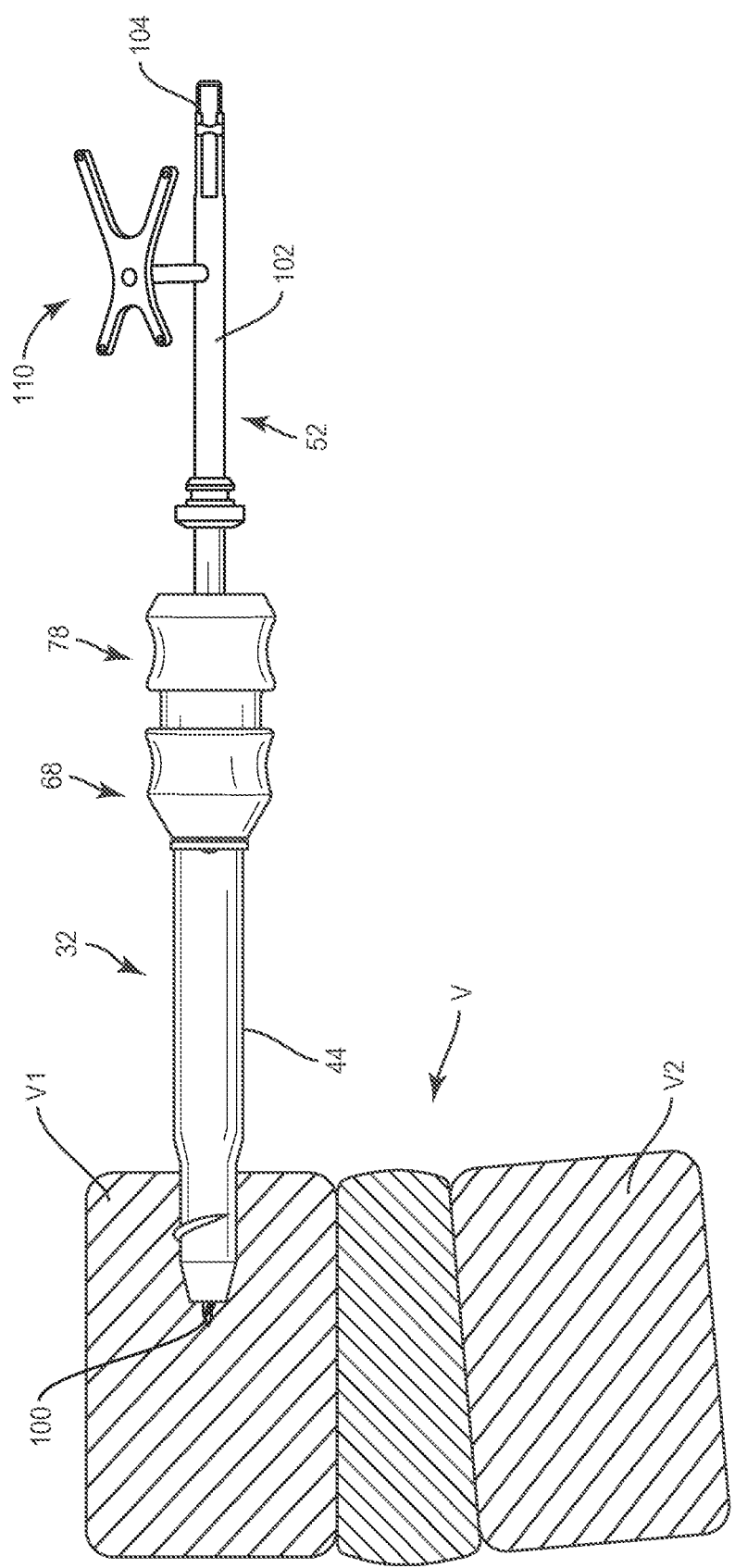
FIG. 19 is a side view of components of the system shown in FIG. 1 disposed with vertebrae.
Figure 20:
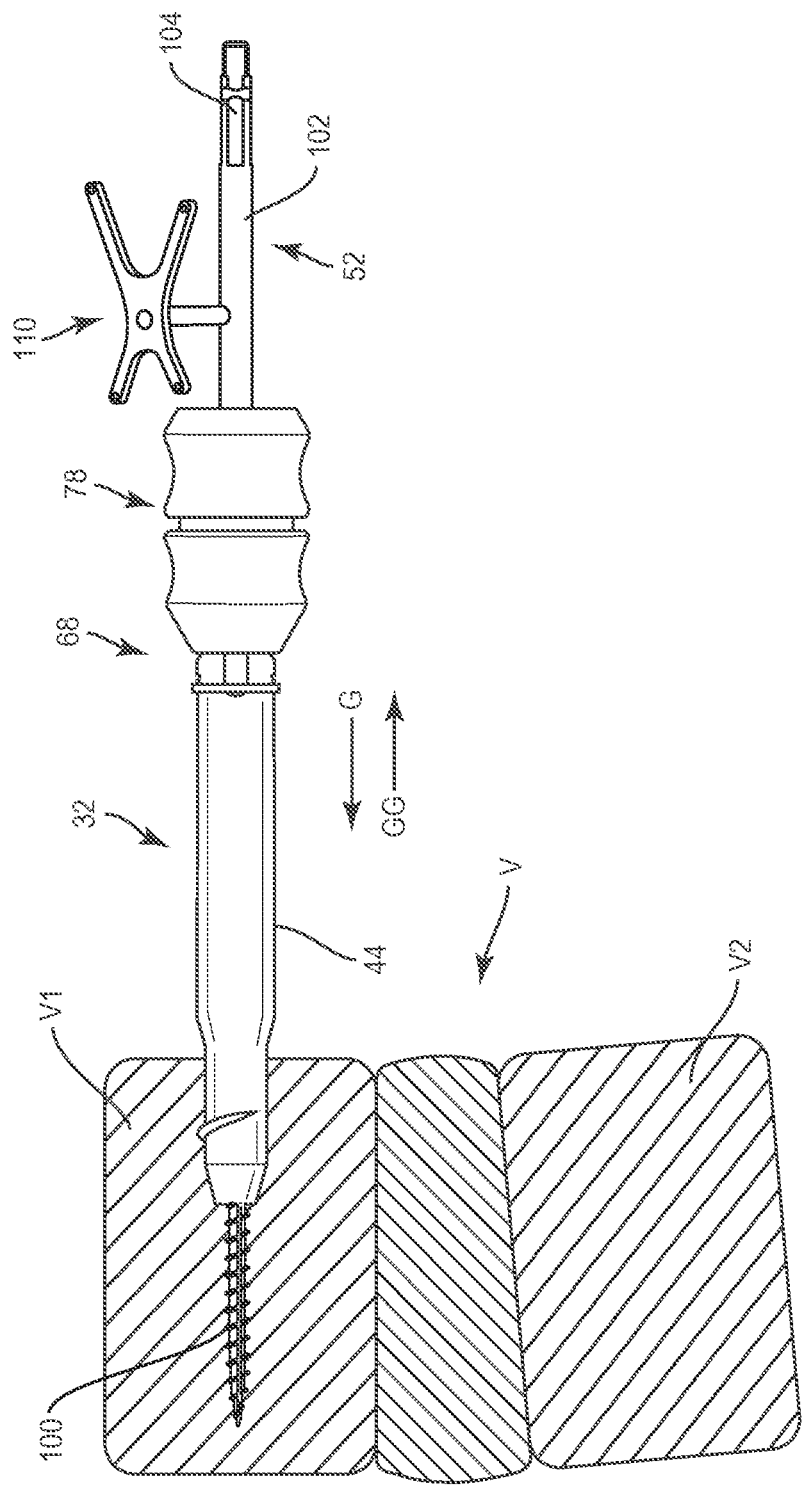
FIG. 20 is a side view of components of the system shown in FIG. 1 disposed with vertebrae.
Figure 21:
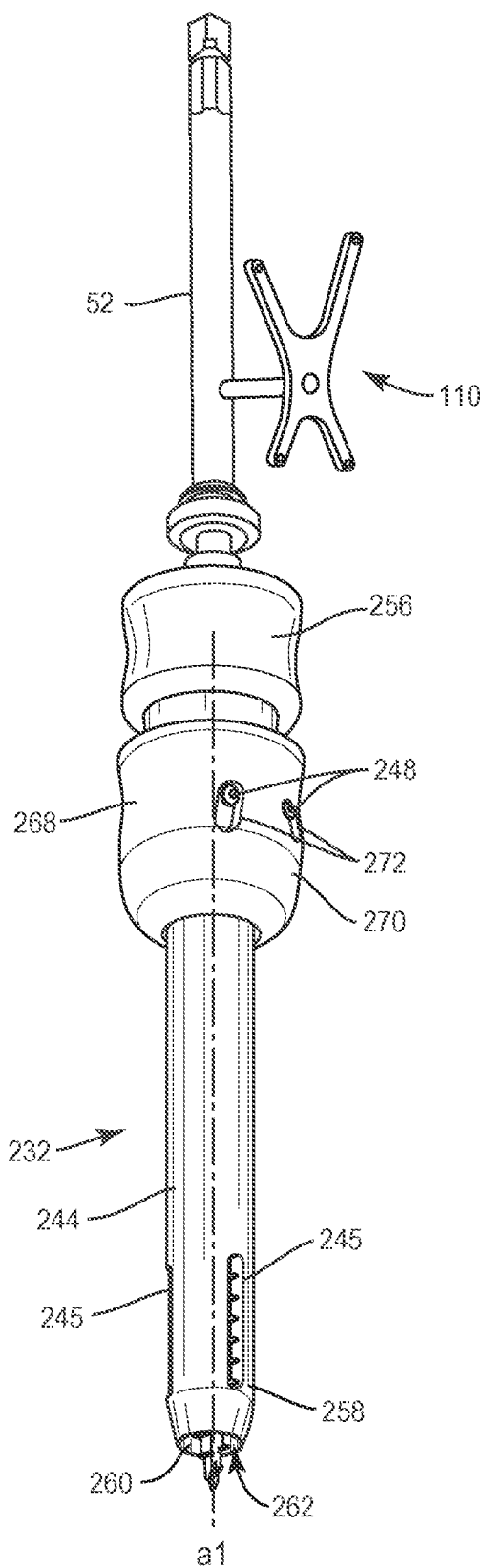
FIG. 21 is a perspective view of components of one embodiment of a surgical implant system in accordance with the principles of the present disclosure.
Figure 22:
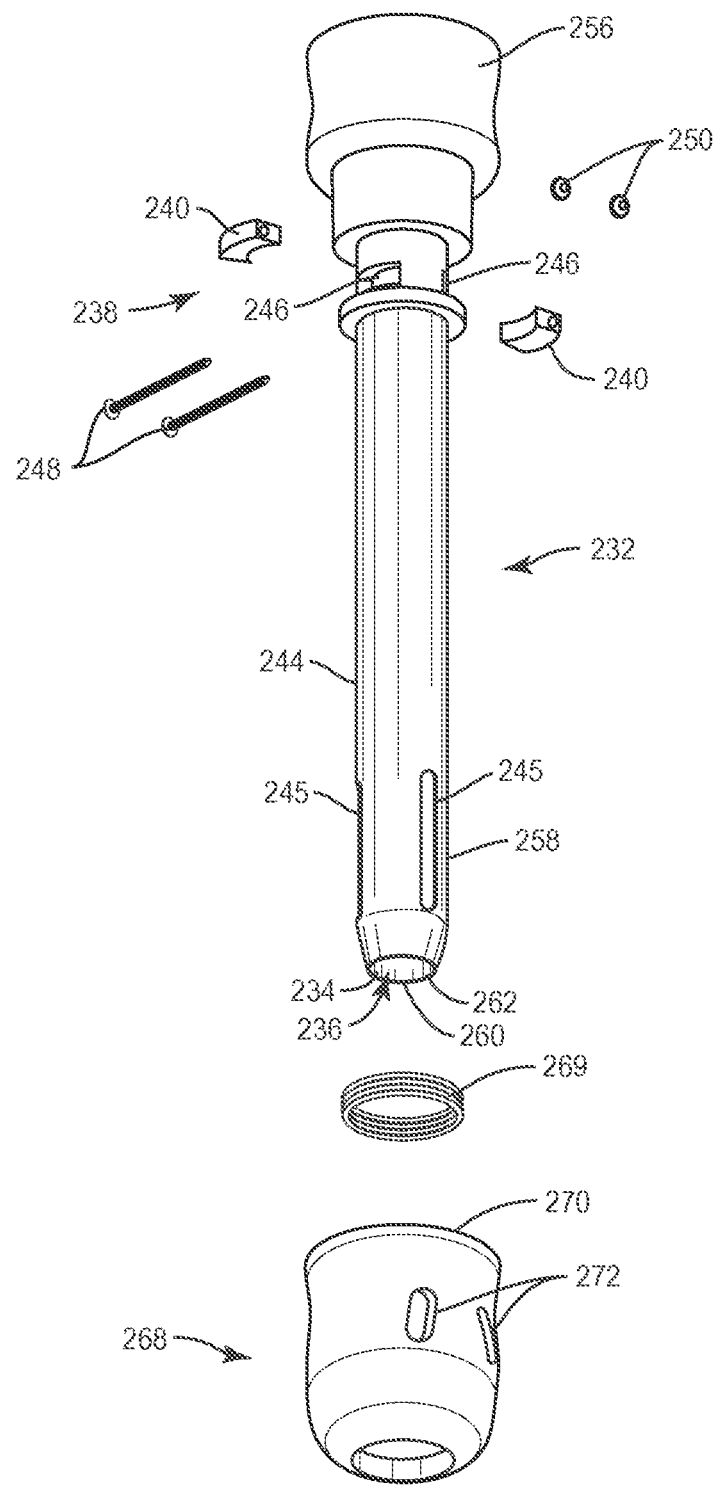
FIG. 22 is a perspective view of components of the system shown in FIG. 21 with parts separated.

In assembly, operation and use, a surgical implant system, similar to system 30 including the surgical instrument described herein, is employed with a surgical procedure for treatment of a spinal disorder affecting a section of a spine of a patient, as discussed herein. For example, the surgical instrument of system 30 can be used with a surgical procedure for treatment of a condition or injury of an affected section of the spine including vertebrae V, as shown in FIGS. 18-20. In some embodiments, one or all of the components of system 30 can be delivered or implanted as a pre-assembled device or can be assembled in situ. System 30 may be completely or partially revised, removed or replaced.

For example, as shown in FIG. 18, the components of system 30 can be employed with a surgical treatment of an applicable condition or injury of an affected section of a spinal column and adjacent areas within a body, such as, for example, vertebrae V. In some embodiments, the components of system 30 may be employed with one or a plurality of vertebra, such as, for example, vertebra V1 and vertebra V2. To treat a selected section of the vertebrae, a medical practitioner obtains access to a surgical site including the vertebrae in any appropriate manner, such as through incision and retraction of tissues. In some embodiments, the components of system 30 can be used in any existing surgical method or technique including open surgery, mini-open surgery, minimally invasive surgery and percutaneous surgical implantation, whereby vertebrae V are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of components of system 30 including the surgical instrument adjacent an area within the patient's body, such as, for example, vertebra V1. Dilator 32 is delivered through the surgical passageway adjacent a surgical site within the patient's body. Tap 52 is positioned within passageway 36 when tabs 40A, 40B are in the non-locking orientation by inserting shaft 96 axially through an opening in end 56, in the direction shown by arrow G, leading with end 98 until groove 106 or groove 108 is aligned with flanges 50. Collar 68 is translated axially relative to surface 44, in the direction shown by arrow G, to move tabs 40A, 40B from the non-locking orientation to the locking orientation such that flanges 50 are disposed within groove 106 or groove 108 and tap 52 is prevented from translating axially relative to dilator 32 within passageway 36. This allows dilator 32 and tap 52 to be delivered through the surgical passageway and to the surgical site in sequence.

Dilator 32 and tap 52 may be delivered through the surgical pathway with shaft 96 in the first locking orientation such that flanges 50 are aligned with groove 108 to maintain screw tap 100 within passageway 36 without extending beyond face 60, as shown in FIG. 18. This configuration allows dilator 32 to be percutaneously navigated through the incision to and from the surgical site including the spine to avoid undesired tearing of soft tissue. Dilator 32 and tap 52 may also be delivered through the surgical pathway with shaft in the second locking orientation such that flanges 50 are aligned with groove 106 and screw tap 100 extends through opening 62 and beyond face 60, as shown in FIG. 19. This configuration, as shown in FIG. 13, allows screw tap 100 to be rotated, in the direction shown by arrow H, or, in the direction shown by arrow HH, to form a shallow aperture in tissue adjacent opening 62 upon delivery to the surgical site.

As dilator 32 and tap 52 are positioned within surgical pathway for delivery to the surgical site, emitter 110 provides signals representative of the position and orientation of tap 52. The signals from emitter 110 and signals from array 112 indicate the position of screw tap 100 relative to the patient's anatomy, as discussed above. In particular, sensor 114 processes the signals from emitter 110 and array 112 to provide information regarding the trajectory of tap 52 relative to a portion of the patient's anatomy and the depth of screw tap 100 within the patient's anatomy by triangulating signals generated by emitter 110 and array 112 to identify the relative position of the reference points provided by array 112 and tap 52. The position and trajectory of tap 52 is compared against the preoperative image data set stored in computer 124 by processor 120, which provides the medical practitioner with a visual representation of the trajectory of tap 52 relative to a portion of the patient's anatomy and the depth of screw tap 100 within the patient's anatomy. Screw tap 100 is fixed axially relative to dilator 32 such that the trajectory and position of tap 52 provides to the medical practitioner information regarding the trajectory and position of dilator 32 that can be used to advance dilator 32 and tap 52 to the surgical site. In some embodiments, the images displayed on monitor 122 will move as dilator 32 and tap 52 are moved within the surgical passageway to provide the medical practitioner real time information regarding the trajectory and position of dilator 32 and tap 52 that can be used to advance dilator 32 and tap 52 to the surgical site.

Once dilator 32 and tap 52 are in the desired location adjacent the surgical site, dilator may be fixed with tissue by rotating dilator 32, in the direction shown by arrow H, which causes portion 64 to penetrate the tissue. This configuration facilitates percutaneous docking of dilator 32 with tissue.

Tabs 40A, 40B are moved from the locking orientation to the non-locking orientation by translating collar 68 relative to surface 44, in the direction shown by arrow GG, such that flanges 50 are spaced apart from grooves 106, 108 to allow tap 52 to translate axially relative to dilator 32 within passageway 36. Tap 52 is rotated, in the direction shown by arrow H, or, in the direction shown by arrow HH, by rotating portion 104 and/or handle 105, which causes tap 100 to penetrate tissue to form a cavity therein. As screw tap 100 is rotated, in the direction shown by arrow H, tap 100 translates axially into vertebra V1, in the direction shown by arrow G, as shown in FIG. 20, thus creating a cavity that is deeper than that created when tabs 40A, 40B are in the first locking orientation and flanges 50 are aligned with groove 106, as shown in FIG. 19. In some embodiments, an actuator can engage portion 104 to rotate tap 52, in the direction shown by arrow H and/or the direction shown by arrow HH.

After the cavity is formed within vertebra V1, dilator 32 and tap 52 may be removed from the patient's body so that an implant, such as, for example, a bone screw can be threaded into the cavity formed by screw tap 100. Prior to removal of dilator 32 and tap 52 from the patient's body, tap 52 is translated axially within passageway 36 such that groove 106 is aligned with flanges 50. Tabs 40 are moved from the non-locking orientation to the locking orientation by translating collar 68 relative to surface 44, in the direction shown by arrow G, such that flanges 50 are disposed in groove 106 to dispose screw tap 100 within passageway 36 without screw tap 100 extending beyond face 60 and to prevent axial translation of tap 52 relative to dilator 32. Dilator 32 and tap 52 may be removed from the patient's body simultaneously while avoiding screw tap 100 from undesired tearing of tissue, such as, for example, soft tissue. In some embodiments, tap 52 may be removed from dilator 32 prior to removal of dilator 32 from the patient's body by translating tap 52 axially, in the direction shown by arrow GG, through the opening in end 56, the surgical pathway and the incision.

Following removal of dilator 32 and tap 52 from the patient's body, a fastener, such as, for example, a bone screw having an external thread configured to engage the surface of the body cavity may be threaded into the cavity in vertebra V1 created by screw tap 100. In some embodiments, the surgical instrument of system 30 can be employed to create one or a plurality of cavities in vertebrae V including vertebra V1, vertebra V2 and/or other vertebra.

In some embodiments, dilator 32 may be employed as a surgical pathway and/or protective sleeve for delivering implants to the surgical site. For example, tap 52 may be removed from dilator 32 prior to removal of dilator 32 from the patient's body by translating tap 52 axially, in the direction shown by arrow GG, through the opening in end 56, the surgical pathway and the incision. Following removal of tap 52 from dilator 32 and the patient's body, an implant, such as, for example, a bone screw is delivered through dilator 32 along passageway 36 to the surgical site for fixation with vertebra V1. A surgical instrument, such as, for example, a driver is introduced through dilator 32 along passageway 36 to the surgical site for engagement with the bone screw. The driver engages the bone screw, which includes an external thread configured to engage the surface of the body cavity and is threaded into the cavity in vertebra V1 created by screw tap 100.

System 30 can include one or a plurality of bone fasteners such as those described herein and/or fixation elements, which may be employed with a single vertebral level or a plurality of vertebral levels. In some embodiments, the bone fasteners may be engaged with vertebrae in various orientations, such as, for example, series, parallel, offset, staggered and/or alternate vertebral levels. In some embodiments, the bone fasteners and/or fixation elements may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts. In some embodiments, system 30 may comprise various instruments including the configuration of the present disclosure, such as, for example, inserters, extenders, reducers, spreaders, distractors, blades, retractors, clamps, forceps, elevators and drills, which may be alternately sized and dimensioned, and arranged as a kit, according to the requirements of a particular application.

In some embodiments, system 30 includes an agent, which may be disposed, packed or layered within, on or about the components and/or surfaces of system 30. In some embodiments, the agent may include bone growth promoting material, such as, for example, bone graft to enhance fixation of the fixation elements with vertebrae V. The components of system 30 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implant components of system 30 are removed from the surgical site and the incision is closed.

In one embodiment, as shown in FIGS. 21-24, system 30, similar to the systems and methods described above with regard to FIGS. 1-20, comprises the surgical instrument, described herein, having a first member, such as, for example, a tissue dilator 232, extending along an axis a1. Dilator 232 has an inner surface 234, similar to surface 34 described above, which defines a cavity, such as, for example, an axial passageway 236, similar to passageway 36 described above, and a locking surface 238, described below, which is transversely movable relative to surface 234. Passageway 236 has a cylindrical cross sectional configuration adapted for movable disposal of tap 52, described above. In some embodiments, tap 52 includes emitter 110, which is employed with components of system 30, as described above.

Dilator 232 extends along axis a1 between an end 256 and an end 258. End 258 includes a distal face 260 extending perpendicular to axis a1 and an opening 262 extending through face 260 that is in communication with passageway 236. End 258 extends in a tapered configuration to face 260. Dilator 232 includes an outer surface 244, similar to surface 44 described above, configured to space apart tissue and is smooth or even to prevent injury to the anatomy of a patient, such as, for example, soft tissue, when dilator 232 is inserted through an incision and delivered to the surgical site. Surface 244 includes a plurality of openings, such as, for example, elongated windows 245 disposed adjacent end 258 and circumferentially about surface 244. In some embodiments, windows 245 facilitate visualization and/or cleaning of tap 52.

Surface 238 includes a pair of movable inserts 240 disposable in substantial alignment with a thickness of dilator 232. Inserts 240 are mounted with dilator 232 and disposed circumferentially about tap 52 in a configuration for disposal with grooves 106 and/or 108, similar to that described above. Surface 244 defines slots 246 disposed circumferentially about dilator 236. Slots 246 are configured for translation of inserts 240 relative to surface 244 in a transverse orientation relative to axis a1. Each insert 240 includes a member, such as, for example, a screw 248 and a washer 250 that facilitate movement of inserts 240 between locking and non-locking orientations of tap 52, similar to that described above and described below. In some embodiments, surface 238 may include one or a plurality of inserts.

Dilator 232 includes a movable collar 268, similar to collar 68 described above, having a wall surface 270. Surface 270 defines slots 272 configured for disposal of screws 248, which are connected to inserts 240. Collar 268 is axially movable along axis a1 between the locking and non-locking orientations such that screws 248 translate along slots 272 at an angular orientation relative to axis a1. This angular translation of screws 248 along slots 272 cause inserts 240 to translate in a transverse orientation relative to axis a1 to move inserts 240 into and out of engagement with grooves 106 and/or 108 of tap 52. Collar 268 is resiliently biased to a locking orientation, as shown in FIG. 23, via a biasing member, such as, for example, a spring 269.

In operation, for example, groove 108 of tap 52 is configured for disposal of inserts 240 to prevent axial translation of tap 52 within passageway 236. Inserts 240 are movable between a locking orientation, as shown in FIG. 23 and similar to the locking orientation described with regard to FIGS. 1-20, and a non-locking orientation, as shown in FIG. 24 and similar to the non-locking orientation described with regard to FIGS. 1-20. In the locking orientation, inserts 240 are disposed with groove 108 to prevent axial translation of tap 52 within passageway 236.

Figure 23:
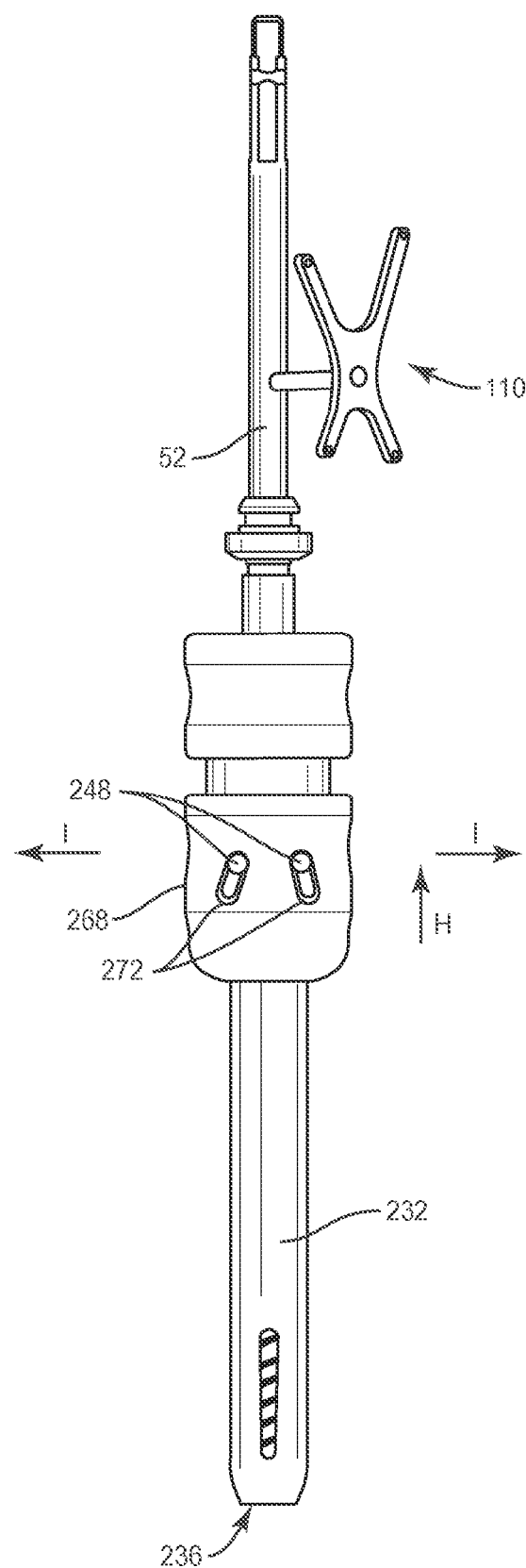
FIG. 23 is a side view of components of the system shown in FIG. 21.
Figure 24:
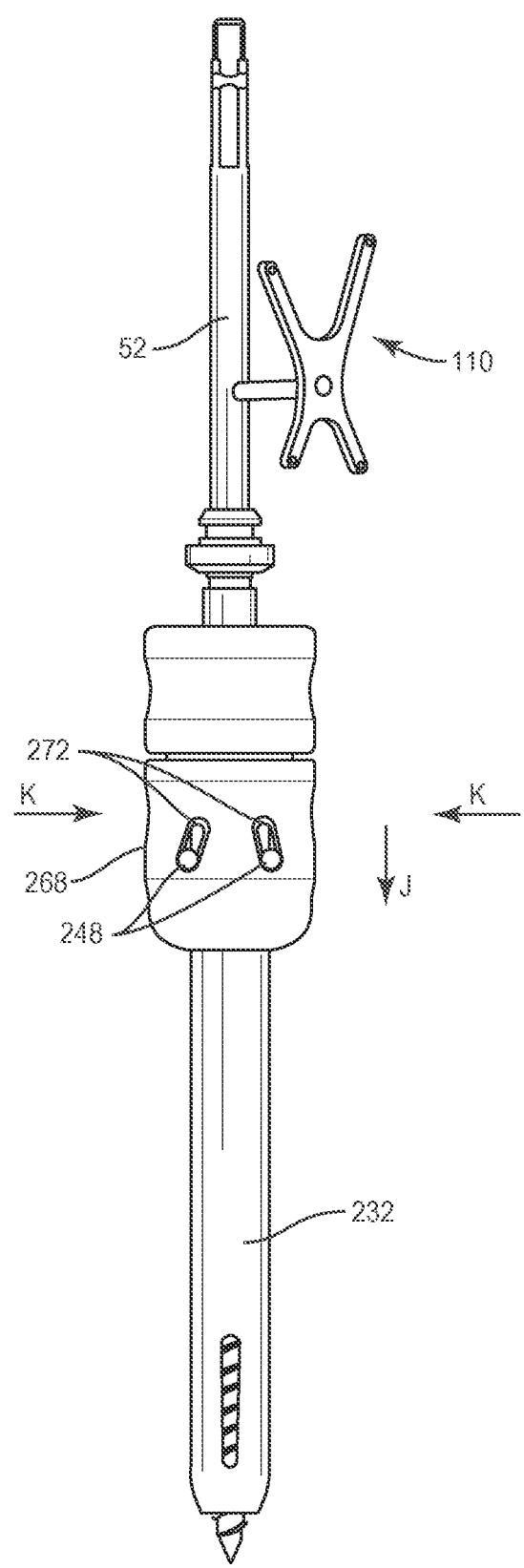
FIG. 24 is a side view of components of the system shown in FIG. 21.

Inserts 240 are movable from the locking orientation to the non-locking orientation by moving collar 268 relative to dilator 232, in the direction shown by arrow H in FIG. 23. Screws 248 translate along slots 272, in an outward orientation, causing inserts 240 to translate, in the direction shown by arrows I, to move inserts 240 out of engagement with groove 108. In the non-locking orientation, as shown in FIG. 24, tap 52 is permitted to translate axially relative to dilator 232 within passageway 236.

Inserts 240 are movable from the non-locking orientation to the locking orientation by releasing collar 268 such that the resilient bias of spring 269 causes collar 268 to move relative to dilator 232, in the direction shown by arrow J in FIG. 24. Screws 248 translate along slots 272, in an inward orientation, causing inserts 240 to translate, in the direction shown by arrows K, to move inserts 240 into engagement with the surfaces of groove 108. Tap 52 is prevented from translating axially relative to dilator 232 within passageway 236.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for treating a spine disorder, the method comprising the steps of:
   providing an instrument comprising
      a first member including an inner surface that defines a cavity and an outer surface being configured to space tissue, the first member further including a handle and a first locking surface,
      a second member configured for disposal within the cavity and extending between a first end configured to penetrate tissue and a second end including an emitter configured to generate a signal representative of a position of the second member, the second member including a second locking surface, and
      a collar having a first portion slidably engageable with the handle and a second portion engageable with the first locking surface;
   providing a tracking device including a sensor that receives the signal and communicates with a processor to generate data for display of an image from a monitor, the image representing position of the second member relative to a body;
   slidably translating the first portion relative to and along the handle such that the second portion engages the first locking surface to dispose the members in a first orientation such that the locking surfaces are engaged to resist relative axial translation of the members;
   spacing the tissue with the first member;
   navigating the second end of the second member to a surgical site adjacent vertebral tissue with the tracking device;

disposing the members in a second orientation such that the locking surfaces are disengaged and the second member is axially translatable relative to the first member; and rotating the second member to create a bore within the vertebral tissue at the surgical site.

2. A method for treating a spine disorder as recited in claim 1, wherein the second member includes a shaft and the second locking surface includes a plurality of axially spaced apart grooves formed in an outer surface of the shaft such that the shaft is selectively disposable in a plurality of first orientations.

3. A method for treating a spine disorder as recited in claim 1, wherein the step of navigating the second end of the second member to the surgical site comprises moving the second end of the second member relative to the body based upon the image representing position of the second member relative to the body.

* * * * *